US007247609B2

(12) United States Patent
Lütolf et al.

(10) Patent No.: US 7,247,609 B2
(45) Date of Patent: Jul. 24, 2007

(54) GROWTH FACTOR MODIFIED PROTEIN MATRICES FOR TISSUE ENGINEERING

(75) Inventors: Matthias Lütolf, Zurich (CH); Jason Schense, Zurich (CH); Jeffrey A. Hubbell, Zurich (CH); Anna Jen, Zurich (CH)

(73) Assignees: Universitat Zurich, Zurich (CH); Eidgenossische Technische Hochschule Zurich, Zurich (CH)

( * ) Notice: Subject to any disclaimer, the term of this patent is extended or adjusted under 35 U.S.C. 154(b) by 492 days.

(21) Appl. No.: 10/325,021

(22) Filed: Dec. 18, 2002

(65) Prior Publication Data

US 2003/0166833 A1    Sep. 4, 2003

Related U.S. Application Data

(63) Continuation-in-part of application No. 10/323,046, filed on Dec. 17, 2002, and a continuation-in-part of application No. 10/024,918, filed on Dec. 18, 2001, now abandoned.

(30) Foreign Application Priority Data

Nov. 7, 2002    (WO) ................... PCT/EP02/12458

(51) Int. Cl.
    *A01N 37/18*    (2006.01)
(52) U.S. Cl. ............. 514/2; 514/17; 530/4; 530/399; 530/300
(58) Field of Classification Search ............ 514/2, 514/17; 530/4, 399, 300
    See application file for complete search history.

(56) References Cited

U.S. PATENT DOCUMENTS

| 4,613,665 | A |   | 9/1986  | Larm |
| 4,810,784 | A |   | 3/1989  | Larm |
| 5,100,668 | A |   | 3/1992  | Edelman et al. |
| 5,171,670 | A |   | 12/1992 | Kronenberg et al. |
| 5,202,247 | A |   | 4/1993  | Kilburn et al. |
| 5,428,014 | A |   | 6/1995  | Labroo et al. |
| 5,504,001 | A |   | 4/1996  | Foster |
| 5,561,982 | A |   | 10/1996 | Tunkel et al. |
| 5,582,862 | A |   | 12/1996 | Reed et al. |
| 5,641,670 | A |   | 6/1997  | Treco et al. |
| 5,693,341 | A |   | 12/1997 | Schroeder et al. |
| 5,773,577 | A |   | 6/1998  | Cappello |
| 5,814,603 | A | * | 9/1998  | Oldenburg et al. ........... 514/12 |
| 5,840,837 | A |   | 11/1998 | Krstenansky et al. |
| 5,877,153 | A |   | 3/1999  | Harris et al. |
| 5,958,874 | A |   | 9/1999  | Clark et al. |
| 6,054,122 | A |   | 4/2000  | MacPhee et al. |
| 6,117,425 | A |   | 9/2000  | MacPhee et al. |
| 6,136,564 | A |   | 10/2000 | Kopetzki et al. |
| 6,197,325 | B1 |  | 3/2001  | MacPhee et al. |
| 6,331,422 | B1 |  | 12/2001 | Hubbell et al. |
| 6,559,119 | B1 |  | 5/2003  | Burgess et al. |

FOREIGN PATENT DOCUMENTS

| DE | 200 10 297    | 8/2000 |
| WO | WO 89/00051   | 1/1989 |
| WO | WO 90/05177   | 5/1990 |
| WO | WO 92/02620   | 2/1992 |
| WO | WO 92/09301   | 6/1992 |
| WO | WO 92/22312   | 12/1992 |
| WO | WO 94/20133   | 9/1994 |
| WO | WO 95/05396   | 2/1995 |
| WO | WO 95/23611   | 9/1995 |
| WO | WO 96/17633   | 6/1996 |
| WO | WO 00/64481   | 11/2000 |
| WO | WO 03/040235  | 5/2003 |

OTHER PUBLICATIONS

Adams, et al., "Roles of ephrinB ligands and EphB receptors in cardiovascular development: demarcation of arterial/venous domains, vascular morphogenesis, and sprouting angiogenesis," *Genes & Development* 13:295-306 (1999).

Baumgartner, et al., "Constitutive expression of phVEGF165 after intramuscular gene transfer promotes collateral vessel development in patients with critical limb ischemia," *Circulation* 97:1114-1123 (1998).

Blaess, et al., "Structural analysis of the sixth immunoglobulin-like domain of mouse neural cell adhesion molecule L1 and its interactions with αvβ3, αIIbβ3, and α5 β1 integrins," *J Neurochem*, 71:2615-2625 (1998).

Brooks, et al., "Requirement of vascular integrin αvβ3 for angiogenesis," *Science* 264:569-571 (1994).

Bruckner, "EphrinB ligands recruit GRIP family PDZ adaptor proteins into raft membrane microdomains," *Neuron* 22:511-524 (1999).

Calderwood, et al., "Integrins and actin filaments: reciprocal regulation of cell adhesion and signaling," *J Biol Chem* 275:22607-22610 (2000).

(Continued)

*Primary Examiner*—Leon B Lankford, Jr.
(74) *Attorney, Agent, or Firm*—Pabst Patent Group LLP

(57) ABSTRACT

Proteins are incorporated into protein or polysaccharide matrices for use in tissue repair, regeneration and/or remodeling and/or drug delivery. The proteins can be incorporated so that they are released by degradation of the matrix, by enzymatic action and/or diffusion. As demonstrated by the examples, one method is to bind heparin to the matrix by either covalent or non-covalent methods, to form a heparin-matrix. The heparin then non-covalently binds heparin-binding growth factors to the protein matrix. Alternatively, a fusion protein can be constructed which contains a crosslinking region such as a factor XIIIa substrate and the native protein sequence. Incorporation of degradable linkages between the matrix and the bioactive factors can be particularly useful when long-term drug delivery is desired, for example in the case of nerve regeneration, where it is desirable to vary the rate of drug release spatially as a function of regeneration, e.g. rapidly near the living tissue interface and more slowly farther into the injury zone. Additional benefits include the lower total drug dose within the delivery system, and spatial regulation of release which permits a greater percentage of the drug to be released at the time of greatest cellular activity.

20 Claims, 2 Drawing Sheets

OTHER PUBLICATIONS

Camarata, et al., "Sustained Release of Nerve Growth Factor from Biodegradable Polymer Microspheres," *Neurosurgery* 30(3) 313-319 (1992).

Cardin, et al., "Molecular Modeling of Protein-Glycosaminoglycan Interactions," *Arteriosclerosis* 9:21-32 (1989).

Conover, et al., "Disruption of Eph/ephrin signaling affects migration and proliferation in the adult subventricular zone," *Nature Neuroscience* 3(11):1091-3324 (2000).

Dalva, et al., "EphB receptors interact with NMDA receptors and regulate excitatory synapse formulation," *Cell* 103:945-956 (2000).

Dedhar & Hannigan, "Integrin cytoplasmic interactions and bidirectional transmembrane signaling," *Current Opinion in Cell Biology* 8:657-669 (1996).

Downs, et al., "Calcium Alginate Beads as a Slow-Release System for Delivering Angiogenic Molecules in Vivo and In Vitro," *Journal of Cellular Physiology* 152:422-429 (1992).

Eliceiri & Cheresh, "The role of $\alpha v$ integrins during angiogenesis: insights into potential mechanisms of action and clinical development," *Journal of Clinical Investigation* 103:1227-1230 (1999).

Fasol, et al., "Experimental use of a modified fibrin glue to induce site-directed angiogenesis from the aorta to the heart," Journal of Thoracic and Cardiovascular Surgery 107:1432-9 (1994).

Felding-Habermann, et al., "A single immunoglobulin-like domain of the human neural cell adhesion molecule L1 supports adhesion by multiple and platelet integrins," *J Cell Biol* 139:1567-1581 (1997).

Feng, et al., "Roles for ephrins in positionally selective synaptogenesis between motor neurons and muscle fibers," *Neuron* 25:295-306 (2000).

Ferrara & Alitalo, "Clinical applications of angiogenic growth factors and their inhibitorsl" *Nature Medicine* 5:1359-1364 (1999).

Ferrara, "Molecular and biological properties of vascular endothelial growth factor," J Mol Med 77:527-543 (1999).

Folkman, "Angiogenesis in cancer, vascular, rheumatoid and other disease," *Nature Medicine* 1:27-31 (1995).

Gale, et al., "Ephrin-B2 selectivity marks arterial vessels and neovascularization sites in the adult, with expression in both endothelial and smooth-muscle cells," *Developmental Biology* 230:151-160 (2001).

Griesler, et al., "Enhanced endothelial of expanded polyethrafluoroethylene grafts by fibroblast growth factor type 1 Pretreatment," *Surgery* 112:244-255 (1992).

Hall, "Molecular properties of fibrin-based matrices for promotion of angiogenesis in vitro," *Microvascular Research* 62:315-326 (2001).

Hall, et al., "Trimerization of cell adhesion molecule L1 mimics clustered L1 expression on the cell surface: Influence on L1-Ligand interactions and on promotion of neurite outgrowth," *J of Neurochemistry* 75:336-346 (2000).

Hammond, et al., "Management of coronary artery disease: Therapeutic options in patients with diabetes," *JACC* 36:355-65 (2000).

Houle & Johnson, "Nerve growth factor (NGF)-treated nitrocellulose enhances and directs the regeneration of adult rat dorsal root axons through intraspinal neural tissue transplants," *Neuroscience Letters* 103:17-23 (1989).

Hubbell, "Bioactive biomaterials" *Curr. Opinion Biotechnol.* 10(2): 123-129 (1999).

Humphries, "Integrin activation: the link between ligand binding and signal transduction," *Curr Opin Cell Biol* 8:632-640 (1996).

Ilan, et al., "Distinct signal transduction pathways are utilized during the tube formation and survival phases of in vitro angiogenesis," *J of Cell Science* 111:3621-3631 (1998).

Ingber & Folkman, "How does extracellular matrix control capillary morphogenesis?" Cell 58:803-805 (1989).

Kang, et al., "Selective stimulation of endothelial cell proliferation with inhibition of smooth muscle cell proliferation by fibroblast growth factor-1 plus heparin delivered from glue suspensions," *Surgery* 118:280-287 (1995).

Lee, et al., "Analysis of affinity and structural selectivity in the binding of proteins to glycosaminoglycans: Development of a sensitive electrophoretic approach," *Biochemistry* 88:2768-2772 (1991).

Lin, et al., "Purification and Initial Characterization of Rat B49 Glial Cell Line-Derived Neurotrophic Factor," *Journal of Neurochemistry* 758-768 (1994).

Lorsordo, et al., "Gene therapy for myocardial angiogenesis. Initial clinical results with direct myocardial injection of phVEGF165 as sole therapy for myocardial ischemia," *Circulation* 98:2800-2804 (1998).

Lyon, et al., "The Interaction of the Transforming Growth Factor-ÿs with Heparin/Heparan Sulfate is Isoform-specific," *The Journal of Biological Chemistry* 272(29):18000-18006 (1997).

Maysinger, et al., "Microencapsulated nerve growth factor: effects on the forebrain neurons following devascularizing cortical lesions," *Neuroscience Letters* 140:71-74 (1992).

Montgomery, et al., "Human neural cell adhesion molecule L1 and Rat homologue NILE are ligands for integrin $\alpha\gamma\beta 3$," *J Cell Biol* 132:475-485 (1996).

Nehls and Herrmann, "The configuration of fibrin clots determine capillary morphogenesis and endothelial cell migratin," *Microvascular Research* 51:347-364 (1996).

Pepper, et al., "Angiogenesis: a paradigm for balanced extracellular proteolysis cell migration and morphogenesis," *Enzyme Protein* 49:138-162 (1996).

Powell, et al., "Controlled Release of nerve growth factor from a polymeric implant," *Brain Research* 515:309-311 (1990).

Reddi, "Role of Morphogeneti c Proteins in Skeletal Tissue Engineering and Regeneration," *Nature Biotechnology* 16:247-252 (1998).

Rosengart, et al., "Angiogenesis Gene Therapy. Phase I assessment of direct intramyocardial administration of an adenovirus expressing phVEGF165 cDNA to individuals with clinically significant severe coronary artery disease," Circulation 100:468-474 (1999).

Ruoslahti & Engvall, "Perspectives series: Cell adhesion in vascular biology," *J Clin Invest* 99:1149-1152 (1997).

Sakata & Aoki, et al., "Cross-linking of $\alpha 2$-plasmin inhibitor to fibrin by fibrin-stabilizing factor," *J Clin Invest* 65:290-297 (1980).

Sakiyama-Elbert and Hubbell, "Controlled release of nerve growth factor from a heparin-containing fibrin-based cell ingrowth matrix" *Journal of Controlled Release* 69:149-158 (2000).

Sakiyama-Elbert, et al., "Development of growth factor fusion proteins for cell-triggered drug delivery" *FASEB J.* 15:1300-1302 (2001).

Schense, et al., "Enzymatic incorporation of bioactive peptides into fibrin matrices enhances neurite extension" *Nature Biotechnology* 18:415-419 (2000).

Schroeder-Tefft et al., "Collagen and heparin matrices for growth factor delivery," *Journal of Controlled Release* 49:291-298 (1997).

Shin, et al., "Expression of EphrinB2 identifies a stable genetic difference between arterial and venous vascular smooth muscle as well as endothelial cells, and of adult neovascularization," *Developmental Biology* 230:139-150 (2001).

Shireman, et al., "Modulation of vascular cell growth by local cytokine delivery from fibrin glue suspendions," *J Vasc Surg* 19:852-62 (1999).

Schumacher, et al., "Induction of neoangiogenesis in ischemic myocardium by human growth factors," *Circulation* 97:645-650 (1998).

Stein, et al., "Eph receptors discriminate specific ligand oligomers to determine alternative signaling complexes, attachment, and assembly responses," *Genes & Development* 12:667-678.

Takeshita, et al., "Therapeutic Angiogenesis. A single intraarterial bolus of vascular endothelial growth factor augments revascularization in a rabbit ischemic hind limb model," J Clin Invest 93:662-670 (1994).

Thompson, et al., "Site-directed neovessel formation in vivo," *Science* 241:1349-1352 (1988).

Wang, et al., "Molecular distinction and angiogenesis interaction between embryonic arteries and veins revealed by ephrin-B2 and its receptor Eph-B4," *Cell* 93:741-753 (1998).

Weatherford, et al., "Vascular endothelial growth factor and heparin in a biologic glue promotes human aortic endothelial cell proliferation with aortic smooth muscle cell inhibition," *Surgery* 433-439 (1996).

Zisch, et al., "Covalently conjugated VEGF-fibrin matrices for endothelialization" *Journal of Controlled Release* 72:101-113 (2001).

Luginbuehl, et al., "Localized delivery of growth factors for bone repair" *European Journal of Pharmaceutics and Biopharmaceutics* 58:197-208 (2004).

Besson, et al., "Synthetic peptide substrates for a conductimetric assay of *Pseudomonas aeruginosa elastase*," *Analytical Biochemistry* 237(0232):216-223 (1996).

Borrajo, et al., "Derivatized Cyclodextrins as peptidometics: Influence on Neurite Growth," *Bioorganic and Medicinal Chemistry Letters* 7:1185-90 (1997).

Coombs, et al. "Directing sequence-specific proteolysis to new targets. The influence of loop size and target sequence on selective proteolysis by tissue-type plasminogen activator and urokinase-type plasminogen activator," *J. Biol. Chem.*273(8):4323-8 (1998).

Dimilla, et al., "Mathematical model for the effects of adhesion and mechanics on cell migration speed," *Biophys. J.* 60(1):15-37 (1991).

Dinbergs, et al., "Cellular response to transforming growth factor-beta 1 and basic fibroblast growth factor depends on release kinetics and extracellular matrix interactions," *J. Biol. Chem.* 271(47):29822-9 (1996).

Edelman, et al., "Basic fibroblast growth factor enhances the coupling of intimal hyperplasia and proliferation of vasa vasorum in injured rat arteries," *J. Clin. Invest.* 89(2):465-73 (1992).

Edelman, et al., "Controlled and modulated release of basic fibroblast growth factor," *Biomaterials.* 12(7):619-26 (1991).

Edelman, et al., "Perivascular and intravenous administration of basic fibroblast growth factor: vascular and solid organ deposition," *Proc. Natl. Acad. Sci. U. S. A.* 90(4):1513-7 (1993).

Edgar, et al., "The heparin-binding domain of laminin is responsible for its effects on neurite outgrowth and neuronal survival," *EMBO J.* 3(7):1463-8 (1984).

Gotz, et al., "Neurotrophin-6 is a new member of the nerve growth factor family," *Nature* 372(6503):266-9 (1994).

Grainger, et al., "Poly(dimethylsiloxane)-poly(ethylene oxide)-heparin block copolymers. I. Synthesis and Characterization," *J. Biomed. Mater Res.* 22(3): 231-249 (1988).

Harada, et al., "Basic fibroblast growth factor improves myocardial function in chronically ischemic porcine hearts," *J. Clin. Invest.* 94(2):623-30 (1994).

Hata, et al., "Binding of lipoprotein lipase to heparin. Identification of five critical residues in two distinct segments of the amino-terminal domain," *J. Biol. Chem.* 268(12):8447-57 (1993).

Haugen, et al, "Central and peripheral neurite outgrowth differs in preference for heparin-binding versus integrin-binding sequences," *J. Neurosci.* 12(6):2034-42 (1992).

Herbert, et al., "Effects of fibinolysis on neurite growth from dorsal root ganglia cultured in two- and three-dimensional fibrin gels," *J. Comp. Neurol.* 365(3):380-91 (1996).

Herbert, et al., "Effects of fibrin-micromorphology on neurite growth from dorsal root ganglia cultured in three-dimensional fibrin gels," *J. Biomed. Mat. Res.* 40(4):551-9 (1998).

Kallapur, et al, "The neural cell adhesion molecule (NCAM) heparin binding domain binds to cell surface heparan sulfate proteoglycans," *J. Neuro. Res.* 33(4):538-48 (1992).

Kaneda, et al., "Midkine, a heparin-binding growth/differentiation factor, exhibits nerve cell adhesion and guidance activity for neurite outgrowth in vitro," *J. Biochem.* 119(6):1150-6 (1996).

Kiguchi, et al., "Altered expression of epidermal growth factor receptor ligands in tumor promoter-treated mouse epidermis and in primary mouse skin tumors induced by an initiation-promotion protocol," *Mol. Carcinog.* 22(2):73-83 (1998).

Kinosaki, et al., "Identification of heparin-binding stretches of a naturally occurring deleted variant of hepatocyte growth factor (dHGF)," *Biochim. Biophys. Acta.* 1384(1):93-102 (1998).

Kleinman, et al., "The laminins: a family of basement membrane glycoproteins important in cell differentiation and tumor metastases," *Vitam. Horm.*47:161-86 (1993).

Lopez, et al., "Basic fibroblast growth factor in a porcine model of chronic myocardial ischemia: a comparison of angiographic, echocardiographic and coronary flow parameters," *J. Pharmacol. Exp. Ther.* 282(1):385-90 (1997).

Lopez, et al., "Local perivascular administration of basic fibroblast growth factor: drug delivery and toxicological evaluation," *Drug Metab. Dispos.* 24(8):922-4 (1996).

Martin & Timpl, "Laminin and other basement membrane components," *Annu. Rev. Cell. Biol.* 3:57-85 (1987).

Massia, et al., "An RGD spacing of 440 nm is sufficient for integrin alpha V beta 3-mediated fibroblast spreading and 140 nm for focal contact and stress fiber formation," *J. Cell. Biol.* 114(5):1089-100 (1991).

McCaffrey, et al., "Transforming growth factor-beta 1 is a heparin-binding protein: identification of putative heparin-binding regions and isolation of heparins with varying affinity for TGF-beta 1," *J. Cell. Physiol.* 152(2):430-40 (1992).

Netzel-Arnett, et al., "Sequence specificities of human fibroblast and neutrophil collagenases," *J. Biol. Chem.* 266(11):6747-55 (1991).

Nolo, et al., "Developmentally regulated neurite outgrowth response from dorsal root ganglion neurons to heparin-binding growth-associated molecule (HB-GAM) and the expression of HB-GAM in the targets of the developing dorsal root ganglion neurites," *Eur. J. Neurosci.* 8(8):1658-65 (1996).

Presta, et al., "Structure-function relationship of basic fibroblast growth factor: site-directed mutagenesis of a putative heparin-binding and receptor-binding region," *Biochem. Biophys. Res. Commun.* 185(3):1098-107 (1992).

Rixon, et al., "Do the non-catalytic polysaccharide-binding domains and linker regions enhance the biobleaching properties of modular xylanases?" *Appl. Microbiol. Biotechnol.* 46(5-6): 514-520 (1996).

Rogers, et al., "Neuron-specific interactions with two neurite-promoting fragments of fibronectin," *J. Neurosci.* 5(2):369-78 (1985).

Sakiyama, et al., "Incorporation of heparin-binding peptides into fibrin gels enhances neurite extension: an example of designer matrices in tissue engineering," *FASEB J* 13(15): 2214-24 (1999).

Sakiyama-Elbert, et al., "Development of fibrin derivatives for controlled release of heparing binding growth factors," *J. Controlled Release* 65(3) 389-402 (2000).

Schense, et al., "Cross-linking exogenous bifunctional peptiedes into fibrin gels with factor XIIIa," *Bioconjug. Chem.* 10(1): 75-81 (1999).

Seibel, et al., Transfection of mitochnondria: strategy towards a gene therapy of mitochondrial DNA diseases, *Nucleic Acids Res.* 23(1): 10-7 (1995).

Sellke, et al., "Basic FGF enhances endothelium-dependent relaxation of the collateral-perfused coronary microcirculation," *Am. J. Physiol.* 267 (4 Pt 2):H1303-11 (1994).

Smith, et al., "Rapid identification of highly active and selective substrates for stromelysin and matrilysin using bacteriophage peptide display libraries," *J. Biol. Chem.* 270(12):6440-9 (1995).

Spillman, et al., "Defining the interleukin-8-binding domain of heparan sulfate," *J. Biol. Chem.* 273(25):15487-93 (1998).

Steffen, et al., "Characterization of cell-associated and soluble forms of connective tissue growth factor (CTGF) produced by fibroblast cells in vitro," *Growth Factors* 15(3):199-213 (1998).

Studier, et al., "Use of T7 RNA polymerase to direct expression of cloned genes," *Methods Enzymol.* 185:60-89 (1990).

Takagi, et al., "Amino acid sequence studies on the alpha chain of human fibrinogen. Location of four plasmin attack points and a covalent cross-linking site," *Biochemistry* 14(23):5149-56 (1975).

Tashiro, et al., "A synthetic peptide containing the IKVAV sequence from the A chain of laminin mediates cell attachment, migration, and neurite outgrowth," *J. Biol. Chem.* 264(27):16174-82 (1989).

Tessler, et al., "Heparin modulates the interaction of VEGF165 with soluble and cell associated flk-1 receptors," *J. Biol. Chem.* 269(17):12456-61 (1994).

Tyler-Cross, et al., "Heparin binding domain peptides of antithrombin III: analysis by isothermal titration calorimetry and circular dichroism spectroscopy," *Protein Sci.* 3(4):620-7 (1994).

Yamada, "Adhesive recognition sequences," *J. Biol. Chem.* 266(20):12809-12 (1991).

Yanish Perron, et al., "Improved M13 phage cloning vectors and host strains: nucleotide sequences of the M13mp18 and pUC19 vectors," *Gene.* 33(1): 103-19 (1985).

Zucker & Katz, "Platelet factor 4: production, structure, and physiologic and immunologic action," *Proc. Soc. Exp. Biol. Med.* 198(2):693-702 (1991).

* cited by examiner

GROWTH FACTOR MODIFIED PROTEIN MATRICES FOR TISSUE ENGINEERING

CROSS-REFERENCE TO RELATED APPLICATIONS (1) This application is a continuation in part of U.S. application Ser. No. 10/323,046, filed Dec. 17, 2002, entitled "Growth Factor Modified Protein Matrices For Tissue Engineering", by Jeffrey A. Hubbell, Jason C. Schense, Shelly E. Sakiyama-Elbert, and Anna Jen;

(2) This application is also a continuation in part of copending U.S. application Ser. No. 10/024,918, filed Dec. 18, 2001, now abandoned entitled "Enzyme-Mediated Modification of Fibrin for Tissue Engineering", by Jeffrey Hubbell, Jason Schense, Andreas Zisch, and Heike Hall; and (3) This application also claims priority to Application No. PCT/EP 02/12458, entitled "Synthetic matrix for controlled cell ingrowth and tissue regeneration", filed Nov. 7, 2002.

FIELD OF THE INVENTION

The invention relates to fusion proteins or peptides which contain PTH and an amino acid sequence that allows for binding interactions to matrices and to the use of fusion proteins or peptides in tissue repair and regeneration, and in the controlled release of PTH.

BACKGROUND OF THE INVENTION

Parathyroid hormone (PTH) is an 84 amino acid peptide that is made and secreted by the parathyroid gland. This hormone plays a primary role in controlling serum calcium levels through its action on various tissues, including bone. Studies in human with various forms of PTH have demonstrated an anabolic effect on bone, what makes them interesting for treatment of osteoporosis and related bone disorders (U.S. Pat. No. 5,747,456 to Chorev, et al. and WO 00/10596 to Eli Lilly & Co.). The parathyroid hormone acts on cells by binding to a cell surface receptor. This receptor is known to be found on osteoblasts, the cells that are responsible for forming new bone.

The N-terminal 34 amino acid domain of the human hormone has been reported to be biologically equivalent to the full length hormone. PTH 1-34 and its mode of action has been first reported in U.S. Pat. No. 4,086,196. Since research has been done on PTH 1-34 and other truncated versions of the native human PTH form, as e.g. PTH1-25, PTH1-31 and PTH1-38 (see e.g. Rixon R H, et al., *J Bone Miner. Res.*, 9 (8): 1179-89 (August 1994).

The mechanism by which PTH influences bone remodeling is complicated, which has led to conflicting results and subsequently, a significant number of studies on the exact mechanisms involved. It has been demonstrated that if PTH is administered systemically in a continuous manner, that the bone density will decrease. In contrast, it has been reported that if the same molecule is administered in pulsatile fashion, the bone density will increase (see e.g. WO 99/31137 to Eli Lilly & Co.). This apparent contradiction can be explained by the mechanism in which PTH modulates bone remodelling and subsequently the observable parameter of bone density. Within mature bone, the PTH receptor has only been shown to be present on the surface of cells of the osteoblast lineage, but not on osteoclasts. The role that PTH plays in bone remodelling is directed through the osteoblasts as opposed to the osteoclasts. However, the cells at different stages of the osteoblast lineage respond differently when they bind to PTH. Therefore, the dramatic differences that are observed when the PTH is administered using different methods can be accounted for by understanding the different effects that the same molecule has on the different cells within the osteoblast lineage.

When PTH binds to a mesenchymal stem cell, the cell is induced to differentiate into a preosteoblast. Thus, by adding PTH to the system, there is an increase in the preosteoblast population. However, these preosteoblast cells have the PTH receptor as well, and the subsequent binding of the PTH to the receptor on these cells leads to a different response. When PTH binds to the preosteoblast, it results in two separate consequences that lead to bone resorption. First, it inhibits the further differentiation of the preosteoblasts into osteoblasts. Second, it increases the secretion of Interluekin 6 (IL-6) from the preosteoblasts. IL-6 both inhibits preosteoblast differentiation as well as increases preosteoclast differentiation into osteoclasts. This dual response from the cells within the osteoblast lineage is what provides the complex reaction between bone remodelling and PTH exposure. If PTH is dosed periodically for short periods of time, then the mesenchymal stem cells are induced to differentiate into osteoblasts. The short dosing periods then prevent the newly formed preosteoblasts from producing IL-6, preventing activation of the osteoclasts. Therefore, during the intervals of dosing, these newly formed preosteoblasts can further differentiate into osteoblasts, resulting in bone formation. However, if a constant dose of PTH is applied, then the preosteoblasts will have the opportunity to begin producing IL-6, thus activating the osteoclasts and inhibiting themselves, leading to the opposite effect: bone resorption.

For tissue repair or regeneration, cells must migrate into a wound bed, proliferate, express matrix components or form extracellular matrix, and form a final tissue shape. Multiple cell populations must often participate in this morphogenetic response, frequently including vascular and nerve cells. Matrices have been demonstrated to greatly enhance, and in some cases have been found to be essential, for this to occur. Approaches have been made in developing matrices from natural or synthetic origins or a mixture of both. Natural cell in-growth matrices are subject to remodeling by cellular influences, all based on proteolysis, e.g. by plasmin (degrading fibrin) and matrix metalloproteinases (degrading collagen, elastin, etc.). Such degradation is highly localized and occurs only upon direct contact with the migrating cell. In addition, the delivery of specific cell signaling proteins such as growth factors is tightly regulated. In the natural model, macroporous cell in-growth matrices are not used, but rather microporous matrices that the cells can degrade, locally and upon demand, as the cells migrate into the matrix. Due to concerns regarding immunogenicity, expensive production, limited availability, batch variability and purification, matrices based on synthetic precursor molecules, such as modified polyethyleneglycol, have been developed for tissue regeneration in and/or on the body.

While much work has been done studying the systemic effects of PTH, research has not explored local or topical administration of PTH. As PTH has a direct anabolic effect on the osteoblast cell lineage, it should have a strong potential to heal bone defects in addition to influencing bone density if presented appropriately within a defect site. Once the defect has been filled with preosteoblasts, if the PTH signal is turned off, the newly formed preosteoblasts can then differentiate into osteoblasts and begin converting the wound bed, first into woven bone tissue and then into a mature bone structure.

It is therefore an object of the present invention to provide PTH in a form that can be bound to a matrix for tissue repair, regeneration, and remodeling.

It is a further object to present a PTH in a form suitable for topical or local administration to a patient to heal bone defects.

SUMMARY OF THE INVENTION

Fusion peptides which contain a parathyroid hormone (PTH) in one domain and a substrate domain capable of being covalently crosslinked to a matrix in another domain and matrices and kits which contain such fusion proteins or peptides are disclosed herein. Fusion proteins covalently bind to natural or synthetic materials to form matrices, which may be used to heal bone defects. Optionally, all of the components for forming the matrix are applied to a bone defect and the matrix is formed at the site of application. The fusion peptide can be incorporated into the matrix such that either the fusion peptide as a whole or just the respective PTH sequence of the first domain is released by degradation of the matrix, by enzymatic and/or hydrolytic action. Also the fusion peptide can contain a degradable linkage between the first and the second domain that contains hydrolytic or enzymatic cleavage sites. In particular the fusion peptide contains PTH in one domain, a substrate domain capable of being covalently crosslinked to a matrix in a second domain, and a degradation site between the first and the second domain. Preferably, the PTH is human PTH, although PTH from other sources, such as bovine PTH, may be suitable. The PTH can be PTH 1-84 (native), PTH 1-38, PTH 1-34, PTH 1-31, or PTH 1-25, or any modified or allelic versions of PTH exhibiting properties, i.e. bone formation, similar to the foregoing. The degradation site allows the rate of delivery to be varied at different locations within the matrix depending on cellular activity at that location and/or within the matrix. Additional benefits include the lower total drug dose within the delivery system, and spatial regulation of release which permits a greater percentage of the drug to be released at the time of greatest cellular activity.

DETAILED DESCRIPTION OF THE INVENTION

Figure 1:
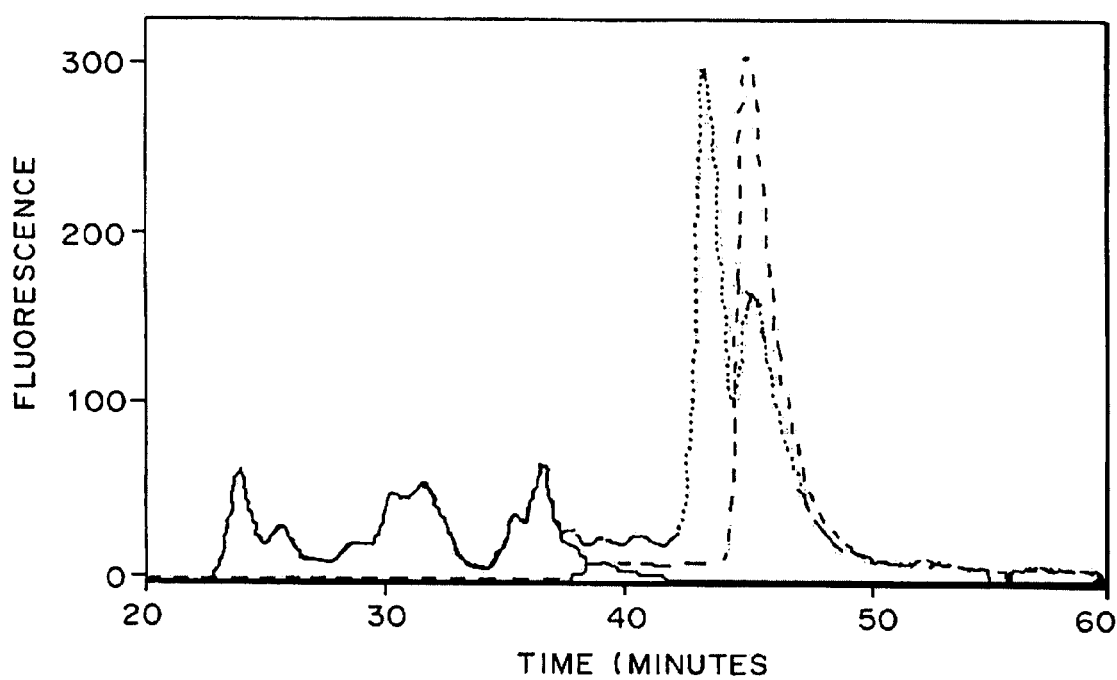
FIG. 1 is a fluorescence detection chromatogram of plasmin-degraded peptide-containing fibrin gels and free peptide. Size exclusion chromatography of a degraded fibrin gel with the $\alpha_2 PI_{1-7}$-$ATIII_{121-134}$ peptide incorporated (-), with the same peptide free added to the degraded fibrin gel containing incorporated peptide ( . . . ), and free peptide alone (--), are shown. The N-terminal leucine residue was dansylated (abbreviated dL). The free peptide eluted at longer times, corresponding to a lower molecular weight, than did the peptide incorporated into the fibrin gel during coagulation, demonstrating covalent attachment to degraded fibrin and thus covalent incorporation via the action of factor XIIIa activity.
Figure 2:
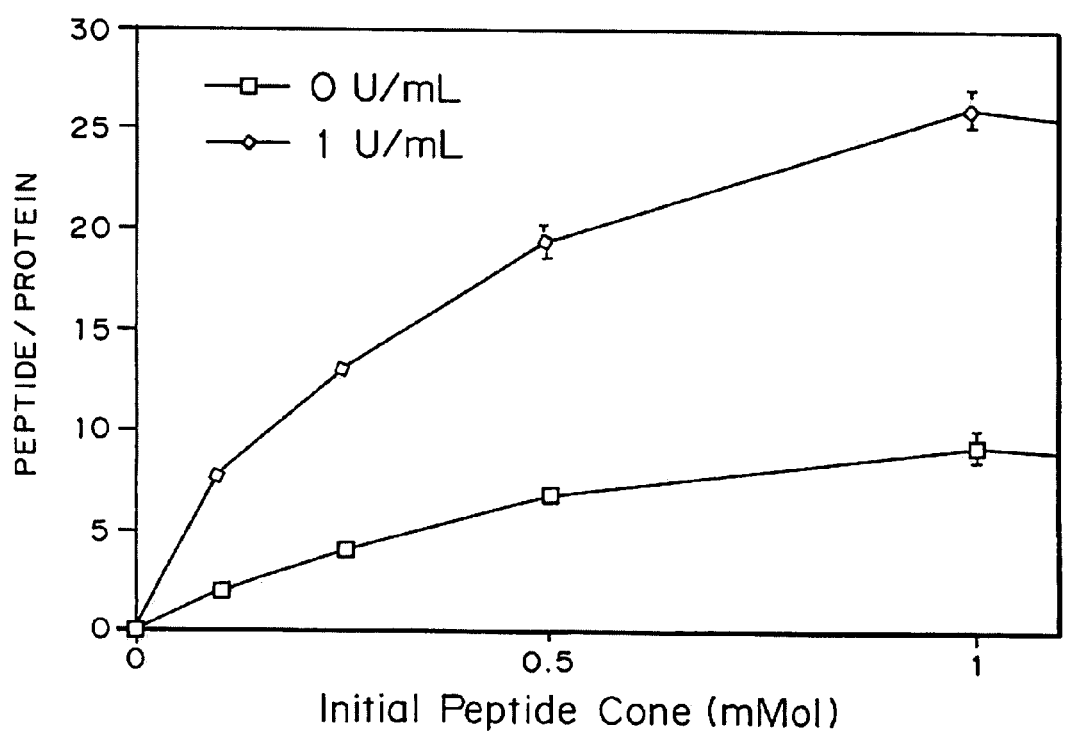
FIG. 2 is a graph of the incorporation of dLNQEQVSPLRGD (SEQ ID NO: 1) into fibrin gels with exogenous Factor XIII added. When 1 U/mL was added, the level of incorporation increased such that more than 25 mol peptide/mol fibrinogen could be achieved.
Figure 3:
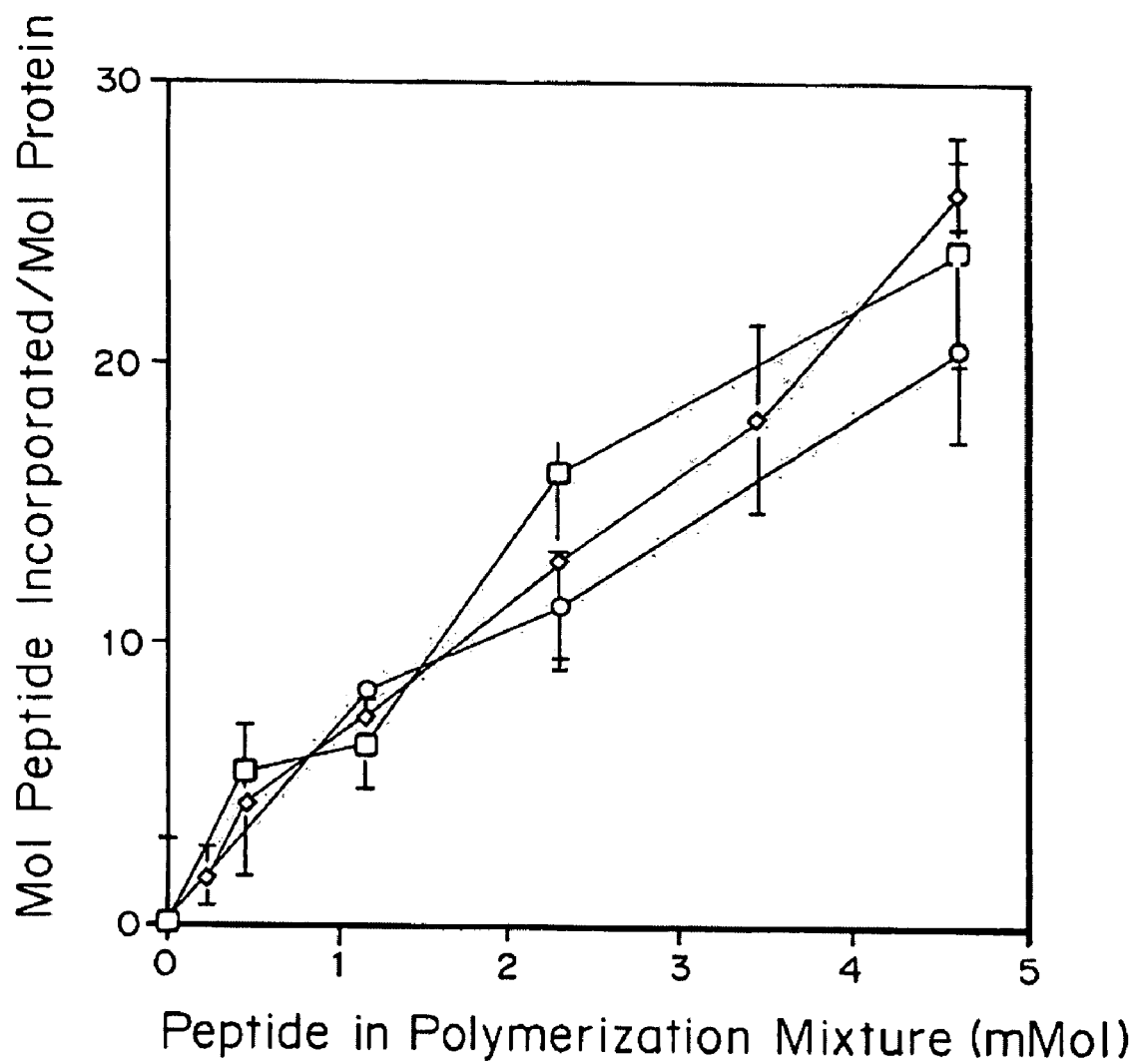
FIG. 3 is a graph of the incorporation of the bidomain peptide, dLNQEQVSPLRGD (SEQ ID NO: 1) into undiluted fibrin glue. Three separate kits were tested and in each case a high level of incorporation could be observed, reaching 25 mol peptide/mol fibrinogen. The concentration of exogenous peptide required for maximal incorporation was at least 5 mM, possibly due to diffusion limitations within the highly dense fibrin matrix that is created. The level of incorporation was very consistent, with each kit providing a similar incorporation profile.

Products and methods for hard tissue repair, regeneration or remodeling, in particular for bone growth, using natural and synthetic matrices having PTH releasably incorporated therein, are described herein. The natural matrices are biocompatible and biodegradable and can be formed in vitro or in vivo, at the time of implantation. PTH can be incorporated into the matrices and retain its full bioactivity. PTH can be releasably incorporated, using techniques that provide control over how and when and to what degree the PTH is released, so that the matrix can be used for tissue repair directly or indirectly, using the matrix as a controlled release vehicle.

Definitions

"Biomaterial" as generally used herein refers to a material intended to interface with biological systems to evaluate, treat, augment, or replace any tissue, organ or function of the body depending on the material either permanently or temporarily. The terms "biomaterial" and "matrix" are used synonymously herein and mean a crosslinked polymeric network which, depending of the nature of the matrix, can be swollen with water but not dissolved in water, i.e. form a hydrogel which stays in the body for a certain period of time fulfilling certain support functions for traumatized or defect hard tissue.

"PTH fusion peptide" as generally used herein refers to a peptide which contains at least a first and a second domain. One domain contains a PTH (native or truncated forms, in particular PTH 1-34) and the other domain contains a substrate domain for being crosslinked to a matrix. An enzymatic or hydrolytic degradation site can also be present between the first and the second domain.

"Strong nucleophile" as generally used herein refers to a molecule which is capable of donating an electron pair to an electrophile in a polar-bond forming reaction. Preferably the strong nucleophile is more nucleophilic than water at physiologic pH. Examples of strong nucleophiles are thiols and amines.

"Conjugated unsaturated bond" as generally used herein refers to the alternation of carbon-carbon, carbon-heteroatom or heteroatom-heteroatom multiple bonds with single bonds, or the linking of a functional group to a macromolecule, such as a synthetic polymer or a protein. Such bonds can undergo addition reactions.

"Conjugated unsaturated group" as generally used herein refers to a molecule or a region of a molecule, which contains an alternation of carbon-carbon, carbon-heteroatom or heteroatom-heteroatom multiple bonds with single bonds, which has a multiple bond which can undergo addition reactions. Examples of conjugated unsaturated groups include, but are not limited to vinyl sulfones, acrylates, acrylamides, quinones, and vinylpyridiniums, for example, 2- or 4-vinylpyridinium and itaconates.

"Synthetic precursor molecules" as generally used herein refers to molecules which do not exist in nature.

"Naturally occurring precursor components or polymers" as generally used herein refers to molecules which could be found in nature.

"Functionalize" as generally used herein refers to modifying a molecule in a manner that results in the attachment of a functional group or moiety. For example, a molecule may be functionalized by the introduction of a molecule which makes the molecule a strong nucleophile or a conjugated unsaturation. Preferably a molecule, for example PEG, is functionalized to become a thiol, amine, acrylate, or quinone. Proteins, in particular, may also be effectively functionalized by partial or complete reduction of disulfide bonds to create free thiols.

"Functionality" as generally used herein refers to the number of reactive sites on a molecule.

"Functionality of the branching points" as generally used herein refers to the number of arms extending from one point in the molecule.

"Adhesion site or cell attachment site" as generally used herein refers to a peptide sequence to which a molecule, for example, an adhesion-promoting receptor on the surface of a cell, binds. Examples of adhesion sites include, but are not limited to, the RGD sequence from fibronectin, and the YIGSR (SEQ ID NO:2) sequence from laminin. Preferably adhesion sites are incorporated into the biomaterial by including a substrate domain crosslinkable to a matrix.

"Biological activity" as generally used herein refers to functional events mediated by a protein of interest. In some embodiments, this includes events assayed by measuring the interactions of a polypeptide with another polypeptide. It also includes assaying the effect which the protein of interest has on cell growth, differentiation, death, migration, adhesion, interactions with other proteins, enzymatic activity, protein phosphorylation or dephosphorylation, transcription, or translation.

"Sensitive biological molecule" as generally used herein refers to a molecule that is found in a cell, or in a body, or which can be used as a therapeutic for a cell or a body, which may react with other molecules in its presence. Examples of sensitive biological molecules include, but are not limited to, peptides, proteins, nucleic acids, and drugs. Biomaterials can be made in the presence of sensitive biological materials, without adversely affecting the sensitive biological materials.

"Regenerate" as generally used herein means to grow back a portion or all of something, such as hard tissue, in particular bone.

"Multifunctional" as generally used herein refers to more than one electrophilic and /or nucleophilic functional group per molecule (i.e. monomer, oligo- and polymer).

"Self selective reaction" as generally used herein means that the first precursor component of a composition reacts much faster with the second precursor component of the composition and vice versa than with other compounds present in a mixture or at the site of the reaction. As used herein, the nucleophile preferentially binds to a electrophile and an electrophile preferentially binds to a strong nucleophile, rather than to other biological compounds.

"Cross-linking" as generally used herein means the formation of covalent linkages. However, it may also refer to the formation of non-covalent linkages, such as ionic bonds, or combinations of covalent and non-covalent likages.

"Polymeric network" as generally used herein means the product of a process in which substantially all of the monomers, oligo- or polymers are bound by intermolecular covalent linkages through their available functional groups to result in one huge molecule.

"Physiological" as generally used herein means conditions as they can be found in living vertebrates. In particular, physiological conditions refer to the conditions in the human body such as temperature, pH, etc. Physiological temperatures means in particular a temperature range of between 35° C. to 42° C., preferably around 37° C.

"Crosslink density" as generally used herein refers to the average molecular weight between two crosslinks ($M_c$) of the respective molecules.

"Equivalent weight" as generally used herein refers to mmol of functional group/g of substance.

"Swelling" as generally used herein refers to the increase in volume and mass by uptake of water by the biomaterial. The terms "water-uptake" and "swelling" are used synonymously throughout this application.

"Equilibrium state" as generally used herein as the state in which a hydrogel undergoes no mass increase or loss when stored under constant conditions in water.

I. Matrices and PTH

A. Matrix Materials

The matrix is formed by crosslinking ionically, covalently, or by combinations thereof precursor molecules to a polymeric network or by swelling one or more polymeric materials, i.e. matrices, to form a polymeric network having sufficient inter-polymer spacing to allow for ingrowth or migration into the matrix of cells.

In one embodiment the matrix is formed of proteins, preferably proteins naturally present in the patient into which the matrix is to be implanted. A particularly preferred matrix protein is fibrin, although matrices made from other proteins, such as collagen and gelatin can also be used. Polysaccharides and glycoproteins may also be used to form the matrix. It is also possible to use synthetic polymers which are crosslinkable by ionic or covalent binding.

Fibrin Matrices

Fibrin is a natural material which has been reported for several biomedical applications. Fibrin has been described as material for cell ingrowth matrices in U.S. Pat. No. 6,331,422 to Hubbell et al. Fibrin gels have been used as sealants because of its ability to bind to many tissues and its natural role in wound healing. Some specific applications include use as a sealant for vascular graft attachment, heart valve attachment, bone positioning in fractures and tendon repair (Sierra, D. H., *Journal of Biomaterials Applications*, 7:309-352 (1993)). Additionally, these gels have been used as drug delivery devices, and for neuronal regeneration (Williams, et al., *Journal of Comparative Neurobiology*, 264:284-290 (1987)). Although fibrin provides a solid support for tissue regeneration and cell ingrowth, there are few active sequences in the monomer that directly enhance these processes.

The process by which fibrinogen is polymerized into fibrin has also been characterized. Initially, a protease cleaves the dimeric fibrinogen molecule at the two symmetric sites. There are several possible proteases than can cleave fibrinogen, including thrombin, reptilase, and protease III, and each one severs the protein at a different site (Francis, et al., *Blood Cells*, 19:291-307, 1993). Once the fibrinogen is cleaved, a self-polymerization step occurs in which the fibrinogen monomers come together and form a non-covalently crosslinked polymer gel (Sierra, 1993). This self-assembly happens because binding sites become exposed after protease cleavage occurs. Once they are exposed, these binding sites in the center of the molecule can bind to other sites on the fibrinogen chains, which are present at the ends of the peptide chains (Stryer, L. *In Biochemistry*, W. H. Freeman & Company, NY, 1975). In this manner, a polymer network is formed. Factor XIIIa, a transglutaminase activated from Factor XIII by thrombin proteolysis, may then covalently crosslink the polymer network. Other transglutaminases exist and may also be involved in covalent crosslinking and grafting to the fibrin network.

Once a crosslinked fibrin gel is formed, the subsequent degradation is tightly controlled. One of the key molecules in controlling the degradation of fibrin is α2-plasmin inhibitor (Aoki, N., *Progress in Cardiovascular Disease*, 21:267-286, 1979). This molecule acts by crosslinking to the α chain of fibrin through the action of Factor XIIIa (Sakata, et al., *Journal of Clinical Investigation*, 65:290-297, 1980). By attaching itself to the gel, a high concentration of inhibitor can be localized to the gel. The inhibitor then acts by preventing the binding of plasminogen to fibrin (Aoki, et al., *Thrombosis and Haemostasis*, 39:22-31, 1978) and inactivating plasmin (Aoki, 1979). The α2-plasmin inhibitor contains a glutamine substrate. The exact sequence has been identified as NQEQVSPL (SEQ ID NO: 12), with the first glutamine being the active amino acid for crosslinking.

It has been demonstrated that bi-domain peptides, which contain a factor XIIIa substrate sequence and a bioactive peptide sequence, can be cross-linked into fibrin gels and that this bioactive peptide retains its cellular activity in vitro (Schense, J. C., et al. (1999) *Bioconj. Chem.* 10:75-81).

Synthetic Matrices

Crosslinking reactions for forming synthetic matrices for application in the body include (i) free-radical polymerization between two or more precursors containing unsaturated double bonds, as described in Hem et al., *J. Biomed. Mater. Res.* 39:266-276 (1998), (ii) nucleophilic substitution reaction such as e.g. between a precursor including an amine group and a precursor including a succinimidyl group as disclosed in U.S. Pat. No. 5,874,500 to Rhee et al., (iii) condensation and addition reactions and (iv) Michael type addition reaction between a strong nucleophile and a conjugated unsaturated group or bond (as a strong electrophile). Particularly preferred is the reaction between a precursor molecule having a thiol or amine group as the nucleophilic group and precursor molecules including acrylate or vinyl sulfone groups as electrophilic groups. Most preferred as the nucleophilic group is the thiol group. Michael type addition reactions are described in WO 00/44808 to Hubbell et al., the content of which is incorporated herein by reference. Michael type addition reactions allow for in situ crosslinking of at least a first and a second precursor component under physiological conditions in a self-selective manner, even in the presence of sensitive biological materials. When one of the precursor components has a functionality of at least two, and at least one of the other precursor components has a functionality greater than two, the system will self-selectively react to form a cross-linked three dimensional biomaterial.

Preferably the conjugated unsaturated groups or conjugated unsaturated bonds are acrylates, vinylsulfones, methacrylates, acrylamides, methacrylamides, acrylonitriles, vinylsulfones, 2- or 4-vinylpyridinium, maleimides, or quinones.

The nucleophilic groups are preferably thiol-groups, amino-groups or hydroxyl-groups. Thiol groups are substantially more reactive than unprotonated amine groups. As previously stated, the pH is an important in this consideration: the deprotonated thiol is substantially more reactive than the protonated thiol. Therefore, the addition reactions involving a conjugated unsaturation, such as an acrylate or a quinone, with a thiol to convert two precursor components into a matrix will often be best carried out most quickly and self-selectively at a pH of approximately 8. At pH of approximately 8, most of the thiols of interest are deprotonated (and thus more reactive) and most of the amines of interest are still protonated (and thus less reactive). When a thiol is used as the first precursor molecule, a conjugate structure that is selective in its reactivity for the thiol relative to amines is highly desirable.

Suitable first and second precursor molecules include proteins, peptides, polyoxyalkylenes, poly(vinyl alcohol), poly(ethylene-co-vinyl alcohol), poly(acrylic acid), poly (ethylene-co-acrylic acid), poly(ethyloxazoline), poly(vinyl pyrrolidone), poly(ethylene-co-vinyl pyrrolidone), poly(maleic acid), poly(ethylene-co-maleic acid), poly(acrylamide), and poly(ethylene oxide)-co-poly(propylene oxide) block copolymers. A particularly preferred precursor molecule is polyethylene glycol.

Polyethylene glycol (PEG) provides a convenient building block. One can readily purchase or synthesize linear (meaning with two ends) or branched (meaning more than two ends) PEGs and then functionalize the PEG end groups to introduce either a strong nucleophile, such as a thiol, or a conjugated structure, such as an acrylate or a vinylsulfone. When these components are either mixed with each other or with a corresponding component in a slightly basic environment, a matrix will be formed by reaction between the first and the second precursor component. A PEG component can be reacted with a non-PEG component, and the molecular weight or hydrophilicity of either component can be controlled to manipulate the mechanical characteristics, the permeability, and the water content of the resulting biomaterial.

These materials are generally useful in medical implants, as described in more detail below. In the formation of matrices, especially matrices that are desired to degrade in vivo, peptides provide a very convenient building block. It is straightforward to synthesize peptides that contain two or more cysteine residues, and this component can then readily serve as the first precursor component with nucleophilic groups. For example, a peptide with two free cysteine residues will readily form a matrix when mixed with a PEG tri-vinylsulfone (a PEG having three arms with vinylsulfones at each of its arms) at physiological or slightly higher pH (e.g., 8 to 9). The gelation can also proceed well at even higher pH, but at the potential expense of self-selectivity. When the two liquid precursor components are mixed together, they react over a period of a few minutes to form an elastic gel, consisting of a network of PEG chains, bearing the nodes of the network, with the peptides as connecting links. The peptides can be selected as protease substrates, so as to make the network capable of being infiltrated and degraded by cells, as is done in a protein-based network, such as in a fibrin matrix. Preferably the sequences in the domains are substrates for enzymes that are involved in cell migration (e.g., as substrates for enzymes such as collagenase, plasmin, metalloproteinase (MMP) or elastase), although suitable domains are not be limited to these sequences. One particularly useful sequence is a substrate for the enzyme plasmin (see Examples). The degradation characteristics of the gels can be manipulated by changing the details of the peptide that serves as the cross-linking nodes. One may make a gel that is degradable by collagenase, but not plasmin, or by plasmin, but not collagenase. Furthermore, it is possible to make the gel degrade faster or slower in response to such an enzyme, simply by changing the amino acid sequence so as to alter the $K_m$ or $k_{cat}$, or both, of the enzymatic reaction. One can thus make a biomaterial that is biomimetic, in that it is capable of being remodeled by the normal remodeling characteristics of cells For example, such a study shows substrate sites for the important protease plasmin. The gelation of the PEG with the peptide is self-selective.

Optionally, biofunctional agents can be incorporated into the matrix to provide chemical bonding to other species (e.g., a tissue surface). Having protease substrates incorporated into the matrix is important when the matrix is formed from PEG vinylsulfone. Other than matrices formed from the reaction of PEG acrylates and PEG thiols, matrices formed from PEG vinylsulfones and PEG thiols do not contain hydrolytically degradable bonds. Therefore, the incorporation of protease substrates allows the matrix to degrade degrade in the body.

The synthetic matrices are operationally simple to form. Two liquid precursors are mixed; one precursor contains a precursor molecule with nucleophilic groups and the other precursor molecule contains the electrophilic groups. Physiological saline can serve as the solvent. Minimal heat is generated by reaction. Therefore, the gelation can be carried out in vivo or in vitro, in direct contact with tissue, without untoward toxicity. Thus polymers other than PEG may be used, either telechelically modified or modified on their side groups.

For most healing indications, the rate of cell ingrowth or migration of cells into the matrix in combination with an adapted degradation rate of the matrix is crucial for the overall healing response. The potential of hydrolytically non-degradable matrices to become invaded by cells is primarily a function of network density. If the existing space between branching points or nodes is too small in relation to the size of the cells or if the rate of degradation of the matrix, which results in creating more space within the matrix, is too slow, a very limited healing response will be observed. Healing matrices found in nature, as e.g. fibrin matrices, which are formed as a response to injury in the body are known to consist of a very loose network which very easily can be invaded by cells. The infiltration is promoted by ligands for cell adhesion which are an integrated part of the fibrin network.

Matrices made from synthetic hydrophilic precursor molecules, like polyethene glycol, swell in aqueous environment after formation of the polymeric network. In order to achieve a sufficiently short gelling time (between 3 to 10 minutes at a pH of between 7 to 8 and a temperature in a range of 36 to 38° C.) and quantitative reaction during in-situ formation of the matrix in the body, the starting concentration of the precursor molecules must be sufficiently high. Under such conditions, swelling after network formation would not take place, and the necessary starting concentrations would lead to matrices too dense for cell infiltration when the matrix is not degradable in aqueous environment. Thus swelling of the polymeric network is important to enlarge and widen the space between the branching points.

Irrespective of the starting concentration of the precursor molecules, hydrogels made from the same synthetic precursor molecules, such as a four arm PEG vinylsulfone and a peptide with SH groups, swell to the same water content in equilibrium state. This means that the higher the starting concentration of the precursor molecules are, the higher the end volume of the hydrogel is when it reaches its equilibrium state. If the space available in the body is too small to allow for sufficient swelling and in particular if the linkage formed from the precursor components are not hydrolytically degradable, the rate of cell infiltration and the healing response will decrease. As a consequence, the optimum between two contradictory requirements for application in the body must be found. Good cell infiltration and subsequent healing responses have been observed with a three-dimensional polymeric network formed from the reaction of a trifunctional branched polymer with at least three arms substantially similar in molecular weight and a second precursor molecule that is at least a bifunctional molecule. The ratio of equivalent weight of the functional groups of the first and second precursor molecules is between 0.9 and 1.1. The molecular weights of the arms of the first precursor molecule, the molecular weight of the second precursor molecule and the functionality of the branching points are selected such that the water content of the resulting polymeric network is between the equilibrium weight % and 92 weight % of the total weight of the polymeric network after completion of water uptake. Preferably the water content is between 93 and 95 weight % of the total weight of the polymeric network and the water after completion of water uptake. Completion of water uptake can be achieved either when the equilibrium concentration is reached or when the space available in the biomaterial does not allow for further volume increase. It is therefore preferred to choose the starting concentrations of the precursor components to be as low as possible. This is true for all swellable matrices but in particular for those matrices which undergo cell-mediated degradation and do not contain hydrolytically degradable linkages in the polymeric network.

The balance between gelling time and low starting concentration in particular for hydrolytically non-degradable gels should to be optimized based on the structure of the precursor molecules. In particular, the molecular weight of the arms of the first precursor molecule, the molecular weight of the second precursor molecule and the degree of branching, i.e. the functionality of the branching points, have to be adjusted accordingly. The actual reaction mechanism has a minor influence on this interplay.

Is the first precursor molecule a three or four arm polymer with a functional group at the end of each arm and is the second precursor molecule a linear bifunctional molecule, preferably a peptide containing at least two cysteine groups, then the molecular weight of the arms of the first precursor molecule and the molecular weight of the second precursor molecule are preferably chosen such that the links between the branching points after formation of the network have a molecular weight in the range of between 10 to 13 kD (under the conditions that the links are linear, not branched), preferably between 11 and 12 kD. This allows for a starting concentration of the sum of first and second precursor molecules in a range of between 8 to 12 weight %, preferably between 9 and 10 weight % of the total weight of the first and second precursor molecule in solution (before network formation). In case the branching degree of the first precursor component is increased to eight and the second precursor molecule is still a linear bifunctional molecule, the molecular weight of the links between the branching points is preferably increased to a molecular weight of between 18 to 24 kDa. In case the branching degree of the second precursor molecule is increased from linear to a three or four arm precursor component the molecular weight, i.e. the length of the links increase accordingly. In a preferred embodiment of the present invention a composition is chosen including as the first precursor molecule a trifunctional three arm 15 kD polymer, i.e. each arm having a molecular weight of 5 kD and as the second precursor molecule a bifunctional linear molecule of a molecular weight in the range of between 0.5 to 1.5 kD, even more preferably around 1 kD. Preferably the first and the second precursor component is a polyethylene glycol.

In a preferred embodiment the first precursor component includes as functional groups conjugated unsaturated groups or bonds, most preferred an acrylate or a vinylsulfone and the functional groups of the second precursor molecule includes a nucleophilic group, preferably a thiol or amino groups. In another preferred embodiment of the present invention the first precursor molecule is a four arm 20 kD (each arm a molecular weight of 5 kDa) polymer having functional groups at the terminus of each arm and the second precursor molecule is a bifunctional linear molecule of a molecular weight in the range of between 1 to 3 kD, preferred between 1.5 and 2 kD. Preferably the first precursor molecule is a polyethylene glycol having vinylsulfone groups and the second precursor molecule is a peptide having cysteine groups. In both preferred embodiments the starting concentration of the sum of first and second precursor molecule ranges from the 8 to 11 weight %, preferably between 9 and 10 weight % of the total weight of the first and second precursor molecule and water (before formation of polymeric network), preferably between 5 and 8 weight % to achieve a gelling time of below 10 minutes. These compositions have a gelling time at pH 8.0 and 37° C. of about 3-10 minutes after mixing.

When the matrix contains hydrolytically degradable linkages, formed e.g. by the preferred reaction between acrylates and thiols, the network density with regard to cell infiltration is especially important in the beginning, but in aqueous environment the linkages will be hydrolyzed and the network will be loosened, to allow for cell infiltration. With an increase in the overall branching degree of the polymeric network the molecular weight of the interlinks, i.e. the length of the links must increase.

B. Cell Attachment Sites

Cells interact with their environment through protein-protein, protein-oligosaccharide and protein-polysaccharide interactions at the cell surface. Extracellular matrix proteins provide a host of bioactive signals to the cell. This dense network is required to support the cells, and many proteins in the matrix have been shown to control cell adhesion, spreading, migration and differentiation (Carey, *Annual Review of Physiology*, 53:161-177, 1991). Some of the specific proteins that have been shown to be particularly active include laminin, vitronectin, fibronectin, fibrin, fibrinogen and collagen (Lander, *Journal of Trends in Neurological Science*, 12:189-195, 1989). Many studies of laminin have been conducted, and it has been shown that laminin plays a vital role in the development and regeneration of nerves in vivo and nerve cells in vitro (Williams, *Neurochemical Research*, 12:851-869, 1987), as well as in angiogenesis.

Some of the specific sequences that directly interact with cellular receptors and cause either adhesion, spreading or signal transduction have been identified.

Laminin, a large multidomain protein (Martin, *Annual Review of Cellular Biology*, 3:57-85, 1987), has been shown to consist of three chains with several receptor-binding domains. These receptor-binding domains include the YIGSR (SEQ ID NO: 2) sequence of the laminin B1 chain (Graf, et al., *Cell*, 48:989-996, 1987; Kleinman, et al., *Archives of Biochemistry and Biophysics*, 272:39-45, 1989; and Massia, et al, *J. of Biol. Chem.*, 268:8053-8059, 1993), LRGDN (SEQ ID NO: 3) of the laminin A chain (Ignatius, et al., *J. of Cell Biology*, 111:709-720, 1990) and PDGSR (SEQ ID NO: 4) of the laminin B1 chain (Kleinman, et al, 1989). Several other recognition sequences for cells have also been identified. These include IKVAV (SEQ ID NO: 5) of the laminin A chain (Tashiro, et al., *J. of Biol. Chem.*, 264:16174-16182, 1989) and the sequence RNIAEIIKDI (SEQ ID NO: 6) of the laminin B2 chain (Liesi, et al., *FEBS Letters*, 244:141-148, 1989). The receptors that bind to these specific sequences have also often been identified. A subset of cellular receptors that has shown to be responsible for much of the binding is the integrin superfamily (Rouslahti, E., *J. of Clin. Investigation*, 87:1-5, 1991). Integrins are protein heterodimers that consist of α and β subunits. Previous work has shown that the tripeptide RGD binds to several β1 and β3 integrins (Hynes, R. O., *Cell*, 69:1-25, 1992; Yamada, K. M., *J. of Biol. Chem.*, 266:12809-12812, 1991), IKVAV (SEQ ID NO: 5) binds to a 110 kDa receptor (Tashiro, et al., *J. of Biol. Chem.*, 264:16174-16182, 1989); Luckenbill-Edds, et al., *Cell Tissue Research*, 279:371-377, 1995), YIGSR (SEQ ID NO: 2) binds to a 67 kDa receptor (Graf, et al., 1987) and DGEA (SEQ ID NO: 7), a collagen sequence, binds to the $\alpha_2\beta_1$ integrin (Zutter & Santaro, *Amer. J. of Patholody*, 137:113-120, 1990). The receptor for the RNIAEIIKDI (SEQ ID NO: 6) sequence has not been reported.

In a further preferred embodiment peptide sites for cell adhesion are incorporated into the matrix, namely peptides that bind to adhesion-promoting receptors on the surfaces of cells into the biomaterials of the present invention. Such adhesion promoting peptides can be selected from the group as described above. Particularly preferred are the RGD sequence from fibronectin, the YIGSR (SEQ ID NO: 2) sequence from laminin. Incorporation of cell attachment sites are a particularly preferred embodiment with synthetic matrices, but can also be included with some of the natural matrices. The incorporation can be done, for example, simply by mixing a cysteine-containing cell attachment peptide with the precursor molecule including the conjugated unsaturated group, such as PEG acrylate, PEG acrylamide or PEG vinylsulfone a few minutes before mixing with the remainder of the precursor component including the nucleophilic group, such as thiol-containing precursor component. If the cell attachment site does not include a cysteine, it can be chemically synthesized to include one. During this first step, the adhesion-promoting peptide will become incorporated into one end of the precursor multiply functionalized with a conjugated unsaturation; when the remaining multithiol is added to the system, a cross-linked network will form. Another important implication of the way that networks are prepared here, is the efficiency of incorporation of pendant bioactive ligands such as adhesion signals. This step has to be quantitative, since, for example, unbound ligands (e.g. adhesion sites) could inhibit the interaction of cells with the matrix. As described later on, the derivatization of the precursor with such pendant oligopeptides is conducted in a first step in stoichiometric large excess (minimum: 40-fold) of multiarmed electrophilic precursors over thiols and is therefore definitely quantitative. Aside from preventing unwanted inhibition, this accomplishment is biologically even more significant: cell behavior is extremely sensitive to small changes in ligand densities and a precise knowledge of incorporated ligands helps to design and understand cell-matrix interactions. Summarized, the concentration of adhesion sites covalently bound into the matrix significantly influences the rate of cell infiltration. For example, for a given hydrogel, a RGD concentration range can be incorporated into the matrix with supports cell ingrowth and cell migration in an optimal way. The optimal concentration range of adhesion sites like RGD is between 0.04 and 0.05 mM and even more preferably 0.05 mM in particular for a matrix having a water content between equilibrium concentration and 92 weight % after termination of water uptake.

Excellent bone healing results can be achieved by keeping the rate of cell migration and the rate of matrix degradation at fast. With regard to the matrix design (in particular PTH 1-34 covalently bound), a four arm polyethyleneglycol with a molecular weight of about 20,000 Da crosslinked with a protease degradation site GCRPQGIWGQDRC (SEQ ID NO: 8) and 0.050 mM GRGDSP (SEQ ID NO: 9) give particularly good cell ingrowth results and healing of bone defects. The starting concentration of PEG and peptide below 10 weight % of the total weight of the molecules and water (before swelling). The gels have a useable consistency and allow the osteoblasts and precursor cell to easily infiltrate the matrix.

The matrix material is preferably biodegradable by naturally present enzymes. The rate of degradation can be manipulated by the degree of crosslinking and the inclusion of protease inhibitors in the matrix.

C. Crosslinkable Substrate Domains

The PTH fusion peptide can be crosslinked and covalently bound to matrices through the crosslinkable substrate domain of the PTH fusion peptide. The kind of substrate domain is dependent on the nature of the matrix. For the incorporation into fibrin matrices transglutaminase substrate domains are particularly preferred. The transglutaminase substrate domain may be a Factor XIIIa substrate domain. This Factor XIIIa substrate domain may be include GAKDV (SEQ ID NO: 10), KKKK (SEQ ID NO: 11), or NQEQVSPL (SEQ ID NO: 12). The coupling between the PTH and the transglutaminase substrate domain can be performed by chemical synthesis.

The transglutaminase substrate domain can be a substrate for a transglutaminase other than Factor XIIIa. The most preferred Factor XIIIa substrate domain has an amino acid sequence of NQEQVSPL (SEQ ID NO: 12) (herein referred to as "TG"). Other proteins that transglutaminase recognizes, such as fibronectin, could be coupled to the transglutaminase substrate peptide.

TABLE 1

Transglutaminase substrate domains

| | |
|---|---|
| SEQ ID NO: 13 | YRGD*TIGEGQQHHLGG* (*SEQ ID NO:13*) A peptide with glutamine at the transglutaminase coupling site in the chain of fibrinogen |
| SEQ ID NO: 14 | *GAKDV* (*SEQ ID NO:14*) A peptide that mimics the lysine coupling site in the chain of fibrinogen |
| SEQ ID NO: 11 | KKKK (SEQ ID NO:11) A peptide with a polylysine at a random coupling site |
| SEQ ID NO: 12 | *NQEQVSPL* (*SEQ ID NO:12*) A peptide that mimics the crosslinking site in α2-plasmin inhibitor (abbreviated TG) |

For the incorporation of PTH into a matrix formed from synthetic precursor components, the PTH fusion peptide or any other peptide to be incorporated must be synthesized with at least one additional cysteine goup (—SH) preferably at the N terminus of PTH as the crosslinkable substrate domain. The cysteine can be either directly attached to the PTH or through a linker sequence. The linker sequence can additionally include an enzymatically degradable amino acid sequence, so that the PTH can be cleaved from the matrix by enzymes in substantially the native form. The free cysteine group reacts with the conjugated unsaturated group of the precursor component in a Michael type addition reaction. In the case of PTH 1-34 the bondage to a synthetic matrix for PTH 1-34 is made possible by attaching an additional amino acid sequence to the N-terminus of PTH $_{1-34}$ that contains at least one cysteine. The thiol group of the cysteine can react with a conjugated unsaturated bond on the synthetic polymer to form a covalent linkage. Possibility (a) only a cysteine is attached to the peptide, in possibility (b) an enzymatically degradable, in particular a plasmin degradable sequence is attached as linker between the cysteine and the peptide. The sequence GYKNR (SEQ ID NO:15) between the first domain and the second domain, the cysteine, makes the linkage plasmin degradable.

Thus the PTH fusion peptides, may be further modified to contain a degradable site between the attachment site, i.e. the second domain (i.e. factor XIIIa substrate domain or the cysteine) and the PTH, i.e. the first domain. These sites may be degradable either by non-specific hydrolysis (i.e. an ester bond) or they may be substrates for specific enzymatic (either proteolytic or polysaccharide degrading) degradation. These degradable sites allow the engineering of more specific release of PTH from matrices like fibrin gels. For example, degradation based on enzymatic activity allows for the release of PTH to be controlled by a cellular process rather than by diffusion of the factor through the gel. The degradable site or linkage is cleaved by enzymes released from cells which invaded the matrix.

The degradation sites allow the PTH to be released with little or no modification to the primary peptide sequence, which may result in higher activity of the factor. In addition, it allows the release of the factor to be controlled by cell specific processes, such as localized proteolysis, rather than diffusion from some porous materials. This allows factors to be released at different rates within the same material depending on the location of cells within the material. This also reduces the amount of total PTH needed, since its release is controlled by cellular processes. Conservation of PTH and its bioavailability are distinct advantages of exploiting cell specific proteolytic activity over the use of diffusion controlled release devices. In one possible explanation for the strong healing of a bone defect with PTH covalently bound to a matrix, it is deemed important that the PTH is administered locally over an extended period of time (i.e. not just a single pulsed dose) but not in a continuous fashion. This is accomplished by a slow degradation, through either enzymatic cleavage or hydrolytic cleavage of the matrix. In this way, the molecule is then delivered through a pseudo-pulsed effect that occurs over a sustained period of time. When a progenitor cell infiltrates the matrix, it will encounter a PTH molecule and can differentiate into a preosteoblast. However, if that particular cell does not continue to liberate bound PTH from the matrix, it will effectively convert into an osteoblast and begin producing bone matrix. Finally, the therapeutic effects of the peptide are localized to the defect region and are subsequently magnified.

Enzymes that could be used for proteolytic degradation are numerous. Proteolytically degradable sites could include substrates for collagenase, plasmin, elastase, stromelysin, or plasminogen activators. Exemplary substrates are listed below. P1-P5 denote amino acids 1-5 positions toward the amino terminus of the protein from the site were proteolysis occurs. P1'-P4' denote amino acids 1-4 positions toward the carboxy terminus of the protein from the site where proteolysis occurs.

TABLE 2

Sample substrate sequences for protease.

| Protease | P5 | P4 | P3 | P2 | P1 | P1' | P2' | P3' | P4' | Reference |
|---|---|---|---|---|---|---|---|---|---|---|
| Plasmin | | L | I | K | M | K | | P | | Takagi and Doolittle, (1975) Biochem. 14:5149–5156 |
| Plasmin | | | N | F | K | S | Q | L | | Takagi and Doolittle, 1975 |
| Stromelysin | Ac | G | P | L | A | L | T | A | L | Smith et al., (1995). 1 Biol. Chem. 270:6440–6449 |
| Stromelysin | Ac | P | F | E | L | R | A | NH$_2$ | | Smith et al., 1995 |
| Elastase | | Z- | A | A | F | A | NH$_2$ | | | Besson et al., (1996) Analytical Biochemistry 237:216–223. |
| Collagenase | | G | P | L | G | I | A | G | P | Netzel-Arnett et al., (1991) J. Biol. Chem.. 266:6747–6755 |
| t-PA | P | H | Y | G | R | S | G | G | | Coombs et al., 1998. J. Biol. Chem. 273:4323–4328 |
| u-PA | P | G | S | G | R | S | A | S | G | Coombs et al., 1998 |

In another preferred embodiment an oligo-ester domain could be inserted between the first and the second domain This could be accomplished using an oligo-ester such as oligomers of lactic acid.

Non-enzymatic degradation substrate can consist of any linkage which undergoes hydrolysis by an acid or base catalyzed mechanism. These substrates can include oligo-esters such as oligomers of lactic or glycolic acid. The rate of degradation of these materials can be controlled through the choice of oligomer.

D. PTH

The term "PTH" as used herein includes the human sequence of PTH 1-84 and all truncated, modified and allelic versions of PTH which exhibit bone formation properties when covalently bound to biodegradable natural or synthetic matrices. Preferred truncated versions of PTH are PTH 1-38, PTH 1-34, PTH 1-31 or PTH 1-25. Most preferred is PTH 1-34. Preferably, the PTH is human PTH, although PTH from other sources, such as bovine PTH, may be suitable.

Methods for Incorporation and/or Release of Bioactive Factors

In one preferred embodiment for incorporation of a PTH within the matrix, the matrix includes fibrin which is formed from fibrinogen, a calcium source and thrombin and the PTH fusion peptide will be incorporated within fibrin during coagulation. PTH fusion peptide is designed as fusion peptide which include two domains, a first and a second one, one domain, the second one, is a substrate for a crosslinking enzyme such as Factor XIIIa. Factor XIIIa is a transglutaminase that is active during coagulation. This enzyme, formed naturally from factor XIII by cleavage by thrombin, functions to attach fibrin chains to each other via amide linkages, formed between glutamine side chains and lysine side chains. The enzyme also functions to attach other peptides to fibrin during coagulation, e.g. the cell attachment sites provided they include a factor XIIIa too. Specifically the sequence NQEQVSP (SEQ ID NO: 16), has been demonstrated to function as an effective substrate for factor XIIIa. As described herein before it is either directly linked to the PTH or it can include a degradation site between the PTH (first domain) and the NQEQVSP (SEQ ID NO: 16) sequence (second domain). As such, the PTH fusion peptide may be incorporated within fibrin during coagulation via a factor XIIIa substrate.

Design of Fusion Proteins for Incorporation

The PTH fusion peptide which includes a first domain including the PTH, a second domain including a substrate domain for a crosslinking enzyme and optionally a degradation site between the first and the second domain can be incorporated into the fibrin gels using several different schemes. Preferably the second domain includes a transglutaminase substrate domain and even more preferably it includes a Factor XIIIa substrate domain. Most preferably the Factor XIIIa substrate domain includes NQEQVSP (SEQ ID NO: 16). When this PTH fusion peptide is present during the polymerization of the fibrinogen, i.e. during formation of the fibrin matrix, it is directly incorporated into the matrix.

The degradation site between the first and the second domain of the PTH fusion peptide can be an enzymatic degradation site as described previously. Preferably the degradation site is cleavable by an enzyme selected from the group consisting of plasmin and matrix metalloproteinase. By careful selection of $K_m$ and $k_{cat}$ of this enzymatic degradation site, degradation could be controlled to occur either before or after the protein matrix and/or by utilizing similar or dissimilar enzymes to degrade the matrix, with the placement of the degradation site being tailored for each type of protein and application. This PTH fusion peptide could be directly cross-linked into the fibrin matrix as described above. However, incorporating an enzymatic degradation site alters the release of the PTH during proteolysis.

When the cell-derived proteases reach the sequestered fusion peptide, they can cleave the engineered protein at the newly formed degradation site. The resulting degradation products would include the liberated PTH, which would now be nearly free of any engineered fusion sequences, as well as any degraded fibrin.

II. Methods of Use

The matrices can be used for repair, regeneration, or remodeling of tissues, and/or release of PTH, prior to or at the time of implantation. In some cases it will be desirable to induce crosslinking at the site of administration to conform the matrix to the tissue at the implantation site. In other cases, it will be convenient to prepare the matrix prior to implantation.

Cells can also be added to the matrix prior to or at the time of implantation, or even subsequent to implantation, either at or subsequent to crosslinking of the polymer to form the matrix. This may be in addition to or in place of crosslinking the matrix to produce interstitial spacing designed to promote cell proliferation or in-growth.

Although in most cases it will be desirable to implant the matrix to promote cell growth or proliferation, in some cases the bioactive factors will be used to inhibit the rate of cell proliferation. A specific application is to inhibit the formation of adhesions following surgery.

III. Methods of Application

In the preferred embodiment, the material is gelled in situ in or on the body. In another embodiment the matrix can be formed outside the body and then applied in the preformed shape. The matrix material can be made from synthetic or natural precursor components. Irrespective of the kind of precursor component used, the precursor components should be separated prior to application of the mixture to the body to prevent combination or contact with each other under conditions that allow polymerization or gelation of the components. To prevent contact prior to administration, a kit which separates the compositions from each other may be used. Upon mixing under conditions that allow polymerization; the compositions form a bioactive factor supplemented three dimensional network. Depending on the precursor components and their concentrations, gelling can occur quasi-instantaneously after mixing. Such fast gellation, makes injection, i.e. squeezing of the gelled material through the injection needle, almost impossible.

In one embodiment the matrix is formed from fibrinogen. Fibrinogen, through a cascade of various reactions gels to form a matrix, when brought in contact with thrombin and a calcium source at appropriate temperature and pH. The three components, fibrinogen, thrombin, and the calcium source, should be stored separately. However, as long as at least one of the three components is kept separated the other two components can be combined prior to administration.

In a first embodiment fibrinogen is dissolved (which may contain additionally aprotinin to increase stability) in a buffer solution at physiological pH (in a range from pH 6.5 to 8.0, preferably from pH 7.0 to 7.5) and stored separately from a solution of thrombin in a calcium chloride buffer (e.g. concentration range of from 40 to 50 mM). The buffer solution for the fibrinogen can be a histidine buffer solution at a preferred concentration of 50 mM including additionally NaCl at a preferred concentration of 150 mM or TRIS buffer saline (preferably at a concentration of 33 mM).

In a preferred embodiment, a kit, which contains a fusion protein, fibrinogen, thrombin, and a calcium source, is provided. Optionally, the kit may contain a crosslinking enzyme, such as Factor XIIIa. The fusion protein contains a bioactive factor, a substrate domain for a crosslinking enzyme and a degradation site between the substrate domain and bioactive factor. The fusion protein may be present in either the fibrinogen or the thrombin solution. In a preferred embodiment the fibrinogen solution contains the fusion protein.

The solutions are preferably mixed by a two way syringe device, in which mixing occurs by squeezing the contents of both syringes through a mixing chamber and/or needle and/or static mixer.

In a preferred embodiment both fibrinogen and thrombin are stored separately in lyophilised form. Either of the two can contain the fusion protein. Prior to use, the tris or histidine buffer is added to the fibrinogen, the buffer may additionally contain aprotinin. The lyophilized thrombin is dissolved in the calcium chloride solution. Subsequently, the fibrinogen and the thrombin solutions are placed in separate containers/vials/syringe bodies and mixed by a two way connecting device, such as a two-way syringe. Optionally, the containers/vials/syringe bodies are bipartited thus having two chambers separated by an adjustable partition which is perpendicular to the syringe body wall. One of the chambers contains the lyophilised fibrinogen or thrombin, while the other chamber contains an appropriate buffer solution. When the plunger is pressed down, the partition moves and releases the buffer into the fibrinogen chamber to dissolve the fibrinogen. Once both fibrinogen and thrombin are dissolved, both bipartite syringe bodies are attached to a two way connecting device and the contents are mixed by squeezing them through the injection needle attached to the connecting device. Optionally, the connecting device contains a static mixer to improve mixing of the contents.

In a preferred embodiment the fibrinogen is diluted eight fold and thrombin is diluted 20 fold prior to mixing. This ratio results in a gelation time of approximately one minute.

In another preferred embodiment, the matrix is formed from synthetic precursor components capable of undergoing a Michael addition reaction. Since the nucleophilic precursor component (the multithiol) only reacts with the multiacceptor component (the conjugated unsaturated group) at basic pH, the three components which have to be stored separately prior to mixing are: the base, the nucleophilic component and the multiacceptor component. Both the multiacceptor and the multithiol component are stored as a solutions in buffers. Both of the compositions can include the cell attachment site and additionally the bioactive molecule. Thus, the first composition of the system can for example include the solution of the nucleophilic component and the second composition of the system can include the solution of the multiacceptor component. Either or both of the two compositions can include the base. In another embodiment, the multiacceptor and the multithiol can be included as solution in the first composition and the second composition can include the base. Connecting and mixing occurs in the same way as previously described for fibrinogen. The bipartite syringe body is equally suitable for the synthetic precursor components. Instead of fibrinogen and thrombin the multiacceptor and multithiol components are stored in pulverized form in one of the chamber and the other chamber containes the basic buffer.

The following examples are included to demonstrate preferred embodiments of the invention. While the compositions and methods have been described in terms of preferred embodiments, it will be apparent to those of skill in the art that variations may be applied to the composition, methods and in the steps or in the sequence of steps of the method described herein without departing from the concept, spirit and scope of the invention.

EXAMPLE 1

Matrices Containing Covalently Bound TGPTH.

Synthesis of TGPTH

PTH 1-34-mer peptide showing similar activity to the whole protein, and proteins of this length can be synthesized by standard solid state peptide synthesis methods.

All peptides were synthesized on solid resin using an automated peptide synthesizer using standard 9-fluorenyl-methyloxycarbonyl chemistry. Peptides were purified by c18 chromatography and analyzed using reverse phase chromatrography via HPLC to determine purity as well as mass spectroscopy (MALDI) to identify the molecular weight of each product. Using this method, the following peptide (herein referred to as "TGPTH") was synthesized: $NH_3$-Asn-Gln-Glu-Gln-Val-Ser-Pro-Leu-Ser-Val-Ser-Glu-Ile-Gln-Leu-Met-His-Asn-Leu-Gly-Lys-His-Leu-Asn-Ser-Met-Glu-Arg-Val -Glu-Trp-Leu-Arg-Lys-Lys-Leu-Gln-Asp-Val-His-Asn-Phe-COOH (SEQ ID NO: 17)

In vivo Results

The activity of TGPTH for enhancing bone regeneration was tested in a TISSUCOL® matrix in a sheep drill hole defect. Eight mm holes that are 12 mm deep were created in the proximal and distal femur and humerus of sheep. These holes were filled with an in situ polymerizing fibrin gel. Defects were left empty, filled with TISSUCOL® or TGPTH was added to TISSUCOL® fibrin at 400 μg/mL before polymerization. In each example in which TISSUCOL® was used, it was diluted four fold from the standard concentration available, leading to a fibrinogen concentration of 12.5 mg/mL.

The defects were allowed to heal for eight weeks. After this healing period, the animals were sacrificed, and the bone samples were removed and analyzed by micro computerized topography (μCT). The percent of the defect volume filled with calcified bony tissue was then determined. When defects were left empty, there was no formation of calcified tissue inside the fibrin matrix. When only a fibrin gel was added, there was practically no bone healing as well. However, with the addition of 400 μg/mL of TGPTH, the level of healing increased dramatically, with the defect filled 35% with calcified bone.

EXAMPLE 2

Healing Response with Modified PTH 1-34 Attached to a Fibrin Matrix

Materials

The modified version of $PTH_{1-34}$ that can be incorporated into a fibrin matrix was been tested for the healing response in the criticial size rat cranial defect.

A fibrin gel was made from TISSUCOL® Kit (Baxter AG, CH-8604 Volketswil/ZH) fibrin sealant precursor components. The fibrinogen was diluted in sterile 0.03M Tris buffered solution (TBS, pH 7.4) to form an approximately 8 mg/mL solution and the thrombin was diluted in sterile 50 mM $CaCl_2$ solution to form a 2 U/mL solution. The final concentration of fibrinogen was 1:8 original TISSUCOL® formulation (about 100 mg/mL) and 1:160 original TISSUCOL® thrombin concentration (about 500 IE/mL). A predetermined amount of TG-pl-$PTH_{1-34}$ or $TGPTH_{1-34}$ was then added to the thrombin, and mixed to form a homogenous concentration.

To form the fibrin gel, the dilute precursors were mixed together by injecting the fibrinogen into the tube containing the thrombin. In case of the sheep drill defect (as described below) this mixture was then injected immediately into a drill defect created in sheep cancellous bone, where a fibrin gel formed within 1-5 minutes. In the first series of animal experiments, the efficacy of a fusion protein containing $PTH_{1-34}$ as the bioactive factor (NQEQVSPLYKNRS-VSEIQLMHNLGKHLNSMERVEWLRKKLQDVHNF, SEQ ID NO:18) in healing cortical bone was tested in a small animal model. The sequence, YKNR (SEQ ID NO:19), makes the linkage plasmin degradable ("TG-pl-$PTH_{1-34}$). The TG-pl-$PTH_{1-34}$ was made by chemical synthesis. Purification was accomplished through reversed phase HPLC (C18 column) by using a TFA as the counter ion which resulted in a final product that was a TFA salt. The purity of the TG-pl-$PTH_{1-34}$ was determined to be 95%.

The healing response was explored at both short (3 weeks) and long healing times (7 weeks) to determine if an enhancement in healing could be observed.

Rat Critical Size Cranial Defect

Rats were anaesthetized and the cranial bone was exposed. The periosteum on the outer surface of the cranium was retracted so that it would not play a role in the healing process, and a single 8 mm round defect was created. This defect size was chosen as it has been previously determined that defects of 8 mm or larger do not spontaneously heal by themselves, and are critical size defects. The defect was then fitted with a preformed fibrin matrix and the animal was allowed to heal for 3 and 7 weeks. The defect region was then explanted and analysed via radiology as well as histology.

Results

When TG-pl-$PTH_{1-34}$ was studied at the 3 week timepoint, the level of healing was very similar to that observed with a fibrin matrix alone. The 3 week timepoint was chosen as an early timepoint as other potent morphogens, including rhBMP-2, showed a strong healing effect by 3 weeks. In contrast, the healing effect for TG-pl-$PTH_{1-34}$ was not observable at this early time point. However, when the longer timepoint (7 weeks) was analysed, a moderate dose dependent improvement was observed in the healing in the critical size rat cranial defect with the addition of modified $PTH_{1-34}$ to fibrin matrices. The results are shown in Table 3. When the high dose of modified $PTH_{1-34}$ was employed, the healing response increased by 65%.

TABLE 3

Healing response in the rat cranial defect with modified PTH

| Sample | Dose (μg/mL) | Time (Days) | Healing (% defect filled with bone) |
|---|---|---|---|
| Fibrin | 0 | 63 | 38 |
| TG-pl-$PTH_{1-34}$ | 10 | 63 | 43 |
| TG-pl-$PTH_{1-34}$ | 200 | 63 | 50 |
| TG-pl-$PTH_{1-34}$ | 500 | 63 | 62 |

These results demonstrate that when $PTH_{1-34}$ when it is incorporated into a fibrin matrix, it retains some activity as evidenced by the modest increase in bone formation.

Sheep Bone Drill Defect

TG-pl-$PTH_{1-34}$ was tested as well in a long bone defect model to test the effect of this hormone on healing bone. In the sheep drill defect model, 8 mm cylindrically drill defects that were approximately 15 mm deep were placed in both the proximal and distal region of the femur and humerus bones.

Since the defect was placed in the epiphysis of the long bones, the defect was surrounded by trabecular bone with a thin layer of cortical bone at the rim of the defect. These defects were then filled with an in situ polymerizing fibrin (about 750 µL) that contained various doses of TG-pl-PTH$_{1-34}$ or TGPTH$_{1-34}$. Animals were allowed to heal for eight weeks and then were sacrificed. The defect was analyzed with µCT and histology.

For this series of experiments, three types of compositions were tested. First, TG-pl-PTH$_{1-34}$ was tested over a large concentration range. Secondly, another modified PTH$_{1-34}$, TGPTH$_{1-34}$ (NQEQVSPLSVSEIQLMHNLGKHLN SMERVEWLRKKLQDVHNF; SEQ ID NO:17) was employed that only had a transglutaminase sequence at the amino terminus, without a degradation site. Thus, TGPTH$_{1-34}$ could only be liberated by degradation of the fibrin matrix itself. TGPTH$_{1-34}$ was produced and purified similar to TG-pl-PTH$_{1-34}$. Purity was determined to be 95%. TGPTH$_{1-34}$ was tested at several concentrations that were similar to the concentrations of TG-pl-PTH$_{1-34}$ to compare efficacy. Finally, matrices were made in the presence of granular material, with either TGPTH$_{1-34}$ or TG-pl-PTH$_{1-34}$. The granular material was a standard tricalcium phosphate/hydroxyapatite mixture which was embedded in the matrix during gelation. The effect of adding these granules on the efficacy of PTH$_{1-34}$ was explored. As a control, unmodified fibrin was tested.

Results

When either of the modified PTH$_{1-34}$ molecules was placed in long bone defects, a significant improvement in the healing response was observed over the use of fibrin matrices (control) alone. Use of fibrin alone resulted in little healing, where only 20% of the original defect was filled with newly formed bone.

TG-pl-PTH$_{1-34}$, was tested in a concentration series from 20-1000 µg/mL. For each dose tested, a significant increase in the healing response was observed. For example, when 100 µg/mL of TG-pl-PTH$_{1-34}$ was used, the healing rate was increased to almost 60%.

In a second series of experiments, TGPTH$_{1-34}$ was tested. The use of TGPTH$_{1-34}$ also increased bone healing. For example, the use of 400 µg/mL improved the healing response to 40%, and 1000 µg/mL increased bony healing to 65%. Thus, the addition of either modified PTH$_{1-34}$ sequence resulted in a stronger healing response than the control.

Finally, when either modified PTH$_{1-34}$ molecule was linked to the matrix and a granule/matrix mixture was employed, the efficacy of the PTH$_{1-34}$ was maintained. This was tested for both TG-pl-PTH$_{1-34}$ (see Table 4) as well as TGPTH$_{1-34}$ (see Table 5).

TABLE 4

Healing of a sheep drill defect with TG-pl-PTH$_{1-34}$ incorporated into a fibrin matrix; Healing time 8 weeks

| Sample | Dose (µg/mL) | Healing (% defect filled with bone) |
| --- | --- | --- |
| Fibrin (Control) | 0 | 20 |
| TG-pl-PTH$_{1-34}$ | 50 | 31.3 |
| TG-pl-PTH$_{1-34}$ | 100 | 59.7 |
| TG-pl-PTH$_{1-34}$ | 400 | 73 |
| TG-pl-PTH$_{1-34}$ | 1000 | 77 |
| TG-pl-PTH$_{1-34}$ 400TCP | 400 | 68 |

TABLE 5

Healing of a sheep drill defect with PTH$_{1-34}$ bound to a fibrin matrix; Healing time 8 weeks

| Sample | Dose (µg/mL) | Healing (% defect filled with bone) |
| --- | --- | --- |
| Fibrin | 0 | 20 |
| TGPTH$_{1-34}$ | 400 | 40 |
| TGPTH$_{1-34}$ | 1000 | 65 |
| TGPTH$_{1-34}$ 400TCP | 400 | 71 |

Histological evaluation showed high infiltration in the original defect of spindle and osteoblast progenitor cells supported on an extracellular matrix. Active osteoids with large rounded osteoblasts were common, and signs of endochondreal ossification (chondrocytes) were observed. By eight weeks, osteoclasts and healthy signs of remodeling could be found. But unlike the results obtained from continuous exposure to systemic PTH, no overt response from osteoclasts was observed and new bone formation was significantly greater than absorption in and around the defect area. No foreign body inflammatory response was detected (i.e. no giant cells and only mild monocyte presence). Granules were still present in samples with added mineral particles.

EXAMPLE 3

Preparation of Precursor Components for Synthetic Matrices.

Preparation of PEG-vinylsulfones

Commercially available branched PEGs (4arm PEG, mol. wt. 14,800, 4arm PEG, mol. wt. 10,000 and 8arm PEG, mol. wt. 20,000; Shearwater Polymers, Huntsville, Ala., USA) were functionalized at the OH-termini.

PEG vinyl sulfones were produced under argon atmosphere by reacting a dichloromethane solution of the precursor polymers (previously dried over molecular sieves) with NaH and then, after hydrogen evolution, with divinylsulfone (molar ratios: OH 1: NaH 5: divinylsulfone 50). The reaction was carried out at room temperature for 3 days under argon with constant stirring. After the neutralization of the reaction solution with concentrated acetic acid, the solution was filtered through paper until clear. The derivatized polymer was isolated by precipitation in ice cold diethylether. The product was redissolved in dichloromethane and reprecipitated in diethylether (with thoroughly washing) two times to remove all excess divinylsulfone. Finally, the product was dried under vacuum. The derivatization was confirmed with $^1$H NMR. The product showed characteristic vinyl sulfone peaks at 6.21 ppm (two hydrogens) and 6.97 ppm (one hydrogen). The degree of end group conversion was found to be 100%.

Preparation of PEG-acrylates

PEG acrylates were produced under argon atmosphere by reacting an azeotropically dried toluene solution of the precursor polymers with acryloyl chloride, in presence of triethylamine (molar ratios: OH 1: acryloyl chloride 2: triethylamine 2.2). The reaction proceeded with stirring overnight in the dark at room temperature. The resulting pale yellow solution was filtered through a neutral alumina bed; after evaporation of the solvent, the reaction product was dissolved in dichloromethane, washed with water, dried over sodium sulphate and precipitated in cold diethyl ether. Yield: 88%; conversion of OH to acrylate: 100% (from $^1$H-NMR analysis)

¹H-NMR (CDCl₃): 3.6 (341H (14800 4arm: 337H theor.), 230 (10000 4arm: 227H theor.), or 210H (20000 8 arm: 227H theor.), PEG chain protons), 4.3 (t, 2H, —CH₂—CH₂—O—CO—CH=CH₂), 5.8 (dd, 1H, CH₂=CHCOO—), 6.1 and 6.4 (dd, 1H, CH₂=CH—COO—) ppm.

FT-IR (film on ATR plate): 2990-2790 (v C—H), 1724 (C=O), 1460 ($v_s$ CH₂), 1344, 1281, 1242, 1097 ($v_{as}$ C—O—C), 952, 842 ($v_s$ C—O—C) cm⁻¹.

Peptide Synthesis

All peptides were synthesized on solid resin using an automated peptide synthesizer (9050 Pep Plus Synthesizer, Millipore, Framingham, USA) with standard 9-fluorenylmethyloxycarbonyl chemistry. Hydrophobic scavengers and cleaved protecting groups were removed by precipitation of the peptide in cold diethyl ether and dissolution in deionized water. After lyophilization, the peptides were redissolved in 0.03 M Tris-buffered saline (TBS, pH 7.0) and purified using HPLC (Waters; Milford, USA) on a size exclusion column with TBS, pH 7.0 as the running buffer.

Matrix Formation by Conjugate Addition Reactions

MMP-sensitive gels formed by conjugate addition with a peptide-linked nucleophile and a PEG-linked conjugated unsaturation that allow proteolytic cell migration The synthesis of gels is accomplished entirely through Michael-type addition reaction of thiol-PEG onto vinylsulfone-functionalized PEG. In a first step, adhesion peptides were attached pendantly (e.g. the peptide Ac-GCGYGRGD-SPG-NH₂ (SEQ ID NO: 20)) to a multiarmed PEG-vinylsulfone and then this precursor was cross-linked with a dithiol-containing peptide (e.g. the MMP substrate Ac-GCRDGPQGIAGFDRCG-NH₂ (SEQ ID NO: 21)). In a typical gel preparation for 3-dimensional in vitro studies, 4arm-PEG-vinylsulfone (mol. wt. 15000) was dissolved in a TEOA buffer (0.3M, pH 8.0) to give a 10% (w/w) solution. In order to render gels cell-adhesive, the dissolved peptide Ac-GCGYGRGDSPG-NH₂ (SEQ ID NO: 20) (same buffer) were added to this solution. The adhesion peptide was allowed to react for 30 minutes at 37° C. Afterwards, the crosslinker peptide Ac-GCRDGPQGIWGQDRCG-NH₂ (SEQ ID NO: 21) was mixed with the above solution and gels were synthesized. The gelation occured within a few minutes, however, the crosslinking reaction was carried out for one hour at 37° C. to guarantee complete reaction.

MMP-non-sensitive gels formed by conjugate addition with a PEG-linked nucleophile and a PEG-linked conjugated unsaturation that allow non-proteolytic cell migration.

The synthesis of gels is also accomplished entirely through Michael-type addition reaction of thiol-PEG onto vinylsulfone-functionalized PEG. In a first step, adhesion peptides were attached pendantly (e.g. the peptide Ac-GCGYGRGDSPG-NH₂ (SEQ ID NO:20)) to a multiarmed PEG-vinylsulfone and then this precursor was crosslinked with a PEG-dithiol (m.w. 3.4 kD). In a typical gel preparation for 3-dimensional in vitro studies, 4arm-PEG-vinylsulfone (mol. wt. 15000) was dissolved in a TEOA buffer (0.3M, pH 8.0) to give a 10% (w/w) solution. In order to render gels cell-adhesive, the dissolved peptide Ac-GCGYGRGDSPG-NH₂ (SEQ ID NO: 20) (in same buffer) were added to this solution. The adhesion peptide was allowed to react for 30 minutes at 37° C. Afterwards, the PEG-dithiol precursor was mixed with the above solution and gels were synthesized. The gelation occured within a few minutes, however, the crosslinking reaction was carried out for one hour at 37° C. to guarantee complete reaction.

Matrix Formation by Condensation Reactions

MMP-sensitive gels formed by condensation reactions with a peptide X-linker containing multiple amines and a electrophilically active PEG that allow proteolytic cell migration MMP-sensitive hydrogels were also created by conducting a condensation reaction between MMP-sensitive oligopeptide containing two MMP substrates and three Lys (Ac-GKGPQGIAGQKGPQGIAGQKG-NH₂ (SEQ ID NO: 22) and a commercially available (Shearwater polymers) difunctional double-ester PEG-N-hydroxysuccinimide (NHS-HBS-CM-PEG-CM-HBA-NHS). In a first step, an adhesion peptides (e.g. the peptide Ac-GCGYGRGDSPG-NH₂) (SEQ ID NO:20) was reacted with a small fraction of NHS-HBS-CM-PEG-CM-HBA-NHS and then this precursor was cross-linked to a network by mixing with the peptide Ac-GKGPQGIAGQKGPQGIAGQKG-NH₂ (SEQ ID NO:22) bearing three ε-amines (and one primary amine). In a typical gel preparation for 3-dimensional in vitro studies, both components were dissolved in 10 mM PBS at pH7.4 to give a 10% (w/w) solution and hydrogels were formed within less then one hour.

In contrast to the present hydrogels formed by Michael-type reaction, the desired self-selectivity in this approach is not guaranteed, since amines present in biological materials like cells or tissues will also react with the difunctional activated double esters. This is also true for other PEGs bearing electrophilic functionalities such as PEG-oxycarbonylimidazole (CDI-PEG), or PEG nitrophenyl carbonate.

MMP-non-sensitive hydrogels formed by condensation reactions with a PEG-amine cross-linker and a electrophilically active PEG that allow non-proteolytic cell migration Hydrogels were also formed by conducting a condensation reaction between commercially available branched PEG-amines (Jeffamines) and the same difunctional double-ester PEG-N-hydroxysuccinimide (NHS-HBS-CM-PEG-CM-HBA-NHS). In a first step, the adhesion peptides (e.g. the peptide Ac-GCGYGRGDSPG-NH₂) (SEQ ID NO:20) was reacted with a small fraction of NHS-HBS-CM-PEG-CM-HBA-NHS and then this precursor was cross-linked to a network by mixing with the multiarm PEG-amine. In a typical gel preparation for 3-dimensional in vitro studies, both components were dissolved in 10 mM PBS at pH7.4 to give a 10% (w/w) solution and hydrogels were formed within less then one hour.

Again, in contrast to the present hydrogels formed by Michael-type reaction, the desired self-selectivity in this approach is not guaranteed, since amines present in biological materials like cells or tissues will also react with the difunctional activated double esters. This is also true for other PEGs bearing electrophilic functionalities such as PEG-oxycarbonylimidazole (CDI-PEG), or PEG nitrophenyl carbonate.

EXAMPLE 4

Bone Regeneration with Synthetic Enzymatically Degradable Matrices

Two different starting concentrations of the enzymatic degradeable gels were employed. In each of these, the concentration of RGD and the active factor (CplPTH at 100 μg/mL) were kept constant. The polymeric network was formed from a four-arm branched PEG functionalized with four vinylsulfone endgroups of a molecular weight of 20 kD (molecular weight of each of the arms 5 kD) and dithiol peptide of the following sequence Gly-Cys-Arg-Asp-(Gly- Pro-Gln-Gly-Ile-Trp-Gly-Gln)-Asp-Arg-Cys-Gly (SEQ ID NO:21). Both precursor components were dissolved in 0.3 M Triethanolamine. The starting concentration of the functionalized PEG (first precursor molecule) and the dithiol peptide (second precursor molecule) were varied. In one case the concentration was 12.6 weight % of the total weight of the composition (first and second precursor component+triethanolamine solution). The 12.6 weight % corresponds to a 10 weight % solution when calculated on bases of only the first precursor component. (100 mg/mL first precursor molecule). The second staring concentration was 9.5 weight % of the total weight of the composition (first and second precursor component+triethanolamine solution) which corresponds to 7.5 weight % on basis of only the first precursor molecule (75 mg/mL first precursor molecule) of total weight. This has the consequence that the amount of dithiol peptide was changed such that the molar ratio between vinyl sulfones and thiols was maintained.

The gel which started from a starting concentration of 12.6 weight % swelled to a concentration of 8.9 weight % of total weight of the polymeric network plus water, thus the matrix had a water content of 91.1. The gel which started from a starting concentration of 9.5 weight % swelled to a final concentration of 7.4 weight % of total weight of the polymeric network plus water, thus had a water content of 92.6.

In order to explore the effect of this change, these materials were tested in the sheep drill defect. Here, a 750 μL defect was placed in the cancellous bone of the diaphyses of the sheep femur and humerus and filled with an in situ gellating enzymatic gel. The following amount of calcified tissue was obtained, determined via μCT, with each group at N=2:

| Starting concentration of gel | Calcified Tissue |
|---|---|
| 12.6% | 2.7% |
| 9.5% | 38.4% |

By making the gels less dense and easier for cell penetration, the resulting healing response with the addition of an active factor was stronger. The effect of having final solid concentrations of below 8.5 weight % is obvious from these results.

Clearly then, the design of the matrix is crucial to enable healing in wound defects. Each of these hydrogels were composed of large chains of polyethylene glycol, endlinked to create a matrix. However, the details of how they were linked, via enzymatic degradation sites, the density of the linkers and several other variables were crucial to enable a functional healing response. These differences were very clearly observed in the sheep drill defect model.

EXAMPLE 5

Bone Formation with Synthetic Hydrolytically Degradable Matrices

PTH 1-34 fusion peptide was tested in a synthetic gel as well in the sheep drill defect model exactly as described for the fibrin matrices. A hydrogel network was created by mixing together acrylated 4arm polyethylene glycol, MW 15,000 (Peg 4*15 Acr) with a linear polyethylene gylcol dithiol of MW 3400. Through a Michael type reaction, when the two components are mixed in a buffer of 0.3M Triethanolamine at pH 8.0, the resulting thiolates that are formed at this pH can then react with the conjugated unsaturation of the acrylate to create a covalent bond. By mixing together multifunctional precursors, such that the combined multi-functionality is greater than or equal to five, a hydrogel is formed. In addition, bioactive factors can be added to the matrix through an identical reaction scheme. In this case, bioactive factors, including cell adhesion motives or morphogenic or mitogenic factors could be bound to the matrix by adding a cysteine, the thiol containing amino acid, to the sequence. Here, we have added a cysteine to the cell adhesion sequence, RGD, and more specifically, RGDSP (SEQ ID NO: 23) as well as to the $PTH_{1-34}$ sequence and both were bound to the matrix via the acrylates in the crosslinker. Subsequently, these newly formed hydrogels, then have numerous esters near a thiol, which has been shown to be hydrolytically unstable. This instability allows the gels to slow degrade and be replaced by newly formed tissue.

These particular gels, hydrolytically degradeable with RGD and PTH covalently bound to the matrix, were tested in the sheep drill defect model to test the ability of matrix bound $C-PTH_{1-34}$ to enhance bone growth. In order to determine the amount of enhancement, 0, 100 and 400 μg/mL of $PTH_{1-34}$ fusion peptide were added to the matrix. When this was done, an increase in bone formation was observed with the addition of $PTH_{1-34}$. In each test the healing response was measured at the same timepoint of eight weeks. This was compared to defects which were left empty. When the synthetic hydrolytically degradable matrix without PTH fusion peptide was employed, the healing response was measured at about 40%. This means that 40% of the original defect volume was filled with newly formed bone tissue. Then, when 400 μg/mL of modified $PTH_{1-34}$ fusion peptide was employed, the healing response increased to approximately 60%. In comparison, when the defects were left empty, approximately 10% was filled with calcified tissue. This data is shown in Table 6 below.

TABLE 6

Healing response with synthetic matrices with and without modified PTH

| Treatment | Healing (% Calcified Tissue) |
|---|---|
| Empty | 10 |
| Hydrolytic Gel | 40 |
| Hydrolytic Gel with 100 μg/mL CPTH | 54 |
| Hydrolytic Gel with 400 μg/mL CPTH | 60 |

In comparison to an empty defect, addition of the hydrolytically degradable peg gel alone had a large effect on bone healing, increasing the amount of calcified tissue by 300%. When PTH 1-34 was linked to this matrix, the healing increased even further with the level being up to 50% higher than when the matrix is employed alone and 500% higher than the level of healing obtained when the defect was left empty.

We claim:

1. A fusion peptide, comprising
a first domain comprising a PTH,
a second domain comprising a covalently crosslinkable substrate domain, wherein the convalently crosslinkable substrate domain is transglutaminase substrate domain, and
an enzymatic degradation site between the first and the second domain.

2. The fusion peptide of claim 1 wherein the PTH is selected from the group consisting of PTH 1-84, PTH 1-38, PTH 1-34, PTH 1-31 and PTH 1-25.

3. The fusion peptide of claim 2 wherein the PTH is PTH 1-34.

4. The fusion peptide of claim 1 wherein the second domain comprises a Factor XIIIa substrate domain.

5. The fusion peptide of claim 4, wherein the Factor XIIIa substrate domain comprises SEQ ID NO:12.

6. The fusion peptide of claim 1, wherein the enzymatic degradation site, is cleaved by an enzyme selected from the group consisting of plasmin and matrix metalloproteinase.

7. A kit comprising
a fusion peptide, comprising
a first domain comprising a PTH,
a second domain comprising a covalently crosslinkable substrate domain, wherein the convalently crosslinkable substrate domain is transglutaminase substrate domain, and
an enzymatic degradation site between the first and the second domain.

8. The kit of claim 7 further comprising fibrinogen, thrombin and a calcium source.

9. The kit of claim 7 wherein the kit further comprises a crosslinking enzyme.

10. The kit of claim 7 wherein the PTH is selected from the group consisting of PTH 1-84, PTH 1-38, PTH 1-34, PTH 1-31 and PTH 1-25.

11. The kit of claim 7 wherein the transglutaminase substrate domain comprises a Factor XIIIa substrate domain.

12. The kit of claim 11, wherein the Factor XIIIa substrate domain comprises SEQ ID NO:12.

13. The kit of claim 7, wherein the enzymatic degradation site, is cleaved by an enzyme selected from the group consisting of plasmin and matrix metalloproteinase.

14. A matrix suitable for cellular growth or in-growth, wherein
at least one fusion peptide is covalently linked to the matrix,
wherein the fusion peptide comprises
a first domain comprising a PTH,
a second domain comprising a covalently crosslinkable substrate domain, wherein the convalently crosslinkable substrate domain is transglutaminase substrate domain, and
an enzymatic degradation site between the first and the second domain.
wherein the fusion peptide is linked to the matrix by the second domain.

15. The matrix of claim 14 wherein the PTH is selected from the group consisting of PTH 1-84, PTH 1-38, PTH 1-34 and PTH 1-25.

16. The matrix of claim 14 wherein the transglutaminase substrate domain comprises a Factor XIIIa substrate domain.

17. The matrix of claim 16, wherein the Factor XIIIa substrate domain comprises SEQ ID NO:12.

18. The matrix of claim 14 wherein the matrix comprises fibrin.

19. The matrix of claim 14 wherein the matrix comprises polyethyleneglycol.

20. A method for making a matrix comprising
providing at least one matrix material capable of forming a crosslinked matrix, wherein the matrix material is selected from the group consisting of proteins and synthetic materials,
adding a fusion peptide to the matrix material wherein the fusion peptide comprises
a first domain comprising a PTH,
a second domain comprising a substrate domain capable of being covalently crosslinked to a matrix, wherein the convalently crosslinkable substrate domain is transglutaminase substrate domain, and
an enzymatic degradation site between the first and the second domain,
and crosslinking the matrix material, such that the fusion peptide is linked to the matrix through the second domain.

* * * * *

UNITED STATES PATENT AND TRADEMARK OFFICE
CERTIFICATE OF CORRECTION

PATENT NO. : 7,247,609 B2
APPLICATION NO. : 10/325021
DATED : July 24, 2007
INVENTOR(S) : Matthias Lutolf et al.

It is certified that error appears in the above-identified patent and that said Letters Patent is hereby corrected as shown below:

Claim 20, column 36, lines 36 and 37, replace "domain is transglutaminase" with --domain is a transglutaminase--.

Signed and Sealed this

Twenty-fifth Day of March, 2008

JON W. DUDAS
*Director of the United States Patent and Trademark Office*

UNITED STATES PATENT AND TRADEMARK OFFICE
CERTIFICATE OF CORRECTION

PATENT NO.        : 7,247,609 B2  
APPLICATION NO. : 10/325021  
DATED             : July 24, 2007  
INVENTOR(S)       : Matthias Lutolf et al.

Page 1 of 1

It is certified that error appears in the above-identified patent and that said Letters Patent is hereby corrected as shown below:

Claim 1, column 35, line 6, replace "domain is transglutaminase" with --domain is a transglutaminase--.
Claim 7, column 35, line 27, replace "domain is transglutaminase" with --domain is a transglutaminase--.
Claim 14, column 36, line 9, replace "domain is transglutaminase" with --domain is a transglutaminase--.

Signed and Sealed this

Second Day of June, 2009

JOHN DOLL  
*Acting Director of the United States Patent and Trademark Office*

SEQUENCE LISTING

```
<160> NUMBER OF SEQ ID NOS: 23
<210> SEQ ID NO 1
<211> LENGTH: 12
<212> TYPE: PRT
<213> ORGANISM: Artificial sequence
<220> FEATURE:
<223> OTHER INFORMATION: bidomain peptide
<220> FEATURE:
<221> NAME/KEY: MOD_RES
<222> LOCATION: (1)..(1)
<223> OTHER INFORMATION: dansyl Leucine

<400> SEQUENCE: 1

Leu Asn Gln Glu Gln Val Ser Pro Leu Arg Gly Asp
1               5                   10

<210> SEQ ID NO 2
<211> LENGTH: 5
<212> TYPE: PRT
<213> ORGANISM: Homo sapiens

<400> SEQUENCE: 2

Tyr Ile Gly Ser Arg
1               5

<210> SEQ ID NO 3
<211> LENGTH: 5
<212> TYPE: PRT
<213> ORGANISM: Homo sapiens

<400> SEQUENCE: 3

Leu Arg Gly Asp Asn
1               5

<210> SEQ ID NO 4
<211> LENGTH: 5
<212> TYPE: PRT
<213> ORGANISM: Homo sapiens

<400> SEQUENCE: 4

Pro Asp Gly Ser Arg
1               5

<210> SEQ ID NO 5
<211> LENGTH: 5
<212> TYPE: PRT
<213> ORGANISM: Homo sapiens

<400> SEQUENCE: 5

Ile Lys Val Ala Val
1               5

<210> SEQ ID NO 6
<211> LENGTH: 10
<212> TYPE: PRT
<213> ORGANISM: Homo sapiens

<400> SEQUENCE: 6

Arg Asn Ile Ala Glu Ile Ile Lys Asp Ile
1               5                   10

<210> SEQ ID NO 7
<211> LENGTH: 4
<212> TYPE: PRT
```

```
<213> ORGANISM: Homo sapiens

<400> SEQUENCE: 7

Asp Gly Glu Ala
1

<210> SEQ ID NO 8
<211> LENGTH: 13
<212> TYPE: PRT
<213> ORGANISM: Homo sapiens

<400> SEQUENCE: 8

Gly Cys Arg Pro Gln Gly Ile Trp Gly Gln Asp Arg Cys
1               5                   10

<210> SEQ ID NO 9
<211> LENGTH: 6
<212> TYPE: PRT
<213> ORGANISM: Homo sapiens

<400> SEQUENCE: 9

Gly Arg Gly Asp Ser Pro
1               5

<210> SEQ ID NO 10
<211> LENGTH: 5
<212> TYPE: PRT
<213> ORGANISM: Homo sapiens

<400> SEQUENCE: 10

Gly Ala Lys Asp Val
1               5

<210> SEQ ID NO 11
<211> LENGTH: 4
<212> TYPE: PRT
<213> ORGANISM: Homo sapiens

<400> SEQUENCE: 11

Lys Lys Lys Lys
1

<210> SEQ ID NO 12
<211> LENGTH: 8
<212> TYPE: PRT
<213> ORGANISM: Homo sapiens

<400> SEQUENCE: 12

Asn Gln Glu Gln Val Ser Pro Leu
1               5

<210> SEQ ID NO 13
<211> LENGTH: 16
<212> TYPE: PRT
<213> ORGANISM: Homo sapiens

<400> SEQUENCE: 13

Tyr Arg Gly Asp Thr Ile Gly Glu Gly Gln Gln His His Leu Gly Gly
1               5                   10                  15

<210> SEQ ID NO 14
<211> LENGTH: 5
<212> TYPE: PRT
<213> ORGANISM: Homo sapiens
```

```
<400> SEQUENCE: 14

Gly Ala Lys Asp Val
1               5

<210> SEQ ID NO 15
<211> LENGTH: 5
<212> TYPE: PRT
<213> ORGANISM: Homo sapiens

<400> SEQUENCE: 15

Gly Lys Tyr Asn Arg
1               5

<210> SEQ ID NO 16
<211> LENGTH: 7
<212> TYPE: PRT
<213> ORGANISM: Homo sapiens

<400> SEQUENCE: 16

Asn Gln Glu Gln Val Ser Pro
1               5

<210> SEQ ID NO 17
<211> LENGTH: 42
<212> TYPE: PRT
<213> ORGANISM: Homo sapiens

<400> SEQUENCE: 17

Asn Gln Glu Gln Val Ser Pro Leu Ser Val Ser Glu Ile Gln Leu Met
1               5                   10                  15

His Asn Leu Gly Lys His Leu Asn Ser Met Glu Arg Val Glu Trp Leu
            20                  25                  30

Arg Lys Lys Leu Gln Asp Val His Asn Phe
        35                  40

<210> SEQ ID NO 18
<211> LENGTH: 46
<212> TYPE: PRT
<213> ORGANISM: Homo sapiens

<400> SEQUENCE: 18

Asn Gln Glu Gln Val Ser Pro Leu Tyr Lys Asn Arg Ser Val Ser Glu
1               5                   10                  15

Ile Gln Leu Met His Asn Leu Gly Lys His Leu Asn Ser Met Glu Arg
            20                  25                  30

Val Glu Trp Leu Arg Lys Lys Leu Gln Asp Val His Asn Phe
            35                  40                  45

<210> SEQ ID NO 19
<211> LENGTH: 4
<212> TYPE: PRT
<213> ORGANISM: Homo sapiens

<400> SEQUENCE: 19

Tyr Lys Asn Arg
1

<210> SEQ ID NO 20
<211> LENGTH: 11
<212> TYPE: PRT
<213> ORGANISM: Homo sapiens
<220> FEATURE:
<221> NAME/KEY: MOD_RES
```

```
<222> LOCATION: (1)..(1)
<223> OTHER INFORMATION: ACETYLATION
<220> FEATURE:
<221> NAME/KEY: MOD_RES
<222> LOCATION: (11)..(11)
<223> OTHER INFORMATION: AMIDATION

<400> SEQUENCE: 20

Gly Cys Gly Tyr Gly Arg Gly Asp Ser Pro Gly
1               5                   10

<210> SEQ ID NO 21
<211> LENGTH: 16
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (16)..(16)
<223> OTHER INFORMATION: AMIDATION

<400> SEQUENCE: 21

Gly Cys Arg Asp Gly Pro Gln Gly Ile Trp Gly Gln Asp Arg Cys Gly
1               5                   10                  15

<210> SEQ ID NO 22
<211> LENGTH: 21
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (21)..(21)
<223> OTHER INFORMATION: AMIDATION

<400> SEQUENCE: 22

Gly Lys Gly Pro Gln Gly Ile Ala Gly Gln Lys Gly Pro Gln Gly Ile
        1               5                   10                  15

Ala Gly Gln Lys Gly
            20

<210> SEQ ID NO 23
<211> LENGTH: 5
<212> TYPE: PRT
<213> ORGANISM: Homo sapiens

<400> SEQUENCE: 23

Arg Gly Asp Ser Pro
1               5
```